United States Patent [19]

Oshima et al.

[11] Patent Number: 5,116,863
[45] Date of Patent: May 26, 1992

[54] DIBENZ[B,E]OXEPIN DERIVATIVE AND PHARMACEUTICAL COMPOSITIONS THEREOF

[75] Inventors: Etsuo Oshima; Toshiaki Kumazawa; Shizuo Otaki; Hiroyuki Obase, all of Shizuoka; Kenji Ohmori, Mishima; Hidee Ishii, Shizuoka; Haruhiko Manabe, Shizuoka; Tadafumi Tamura, Shizuoka; Katsuichi Shuto, Shizuoka, all of Japan

[73] Assignee: Kyowa Hakko Kogyo Co., Ltd., Tokyo, Japan

[21] Appl. No.: 20,900

[22] Filed: Mar. 2, 1987

[30] Foreign Application Priority Data

Mar. 3, 1986 [JP] Japan .................................. 61-45676

[51] Int. Cl.$^5$ .................. A61K 31/335; C07D 313/12
[52] U.S. Cl. ........................... 514/450; 548/215; 548/525; 549/354; 514/212; 514/228.2; 514/232.8; 514/253; 514/320; 514/374; 514/422; 540/596; 540/600; 544/62; 544/137; 544/147; 544/369; 544/375; 544/58.7; 546/196
[58] Field of Search .............. 540/596, 602; 544/62, 544/137, 147, 369, 375, 98.7; 546/196; 548/215, 525; 549/354; 514/212, 222, 233, 234, 236, 237, 253, 320, 374, 422, 450, 228.2, 232.8

[56] References Cited

U.S. PATENT DOCUMENTS

| | | | |
|---|---|---|---|
| 3,354,155 | 11/1967 | Tretter | 549/354 X |
| 3,420,851 | 1/1969 | Bloom et al. | 549/354 |
| 3,509,176 | 4/1970 | Winter et al. | 260/333 |
| 4,282,365 | 8/1981 | Rokach | 548/252 |
| 4,396,550 | 8/1983 | Takizawa | 549/354 |
| 4,465,835 | 8/1984 | Takizawa | 546/133 |
| 4,585,788 | 4/1986 | Helsley et al. | 549/354 |
| 4,596,804 | 6/1986 | Takizawa | 514/253 |
| 4,871,865 | 10/1989 | Lever et al. | 549/354 |
| 4,923,892 | 5/1990 | Lever et al. | 514/450 |

FOREIGN PATENT DOCUMENTS

| | | |
|---|---|---|
| 0069810 | 1/1983 | European Pat. Off. . |
| 0085870 | 8/1983 | European Pat. Off. . |
| 0130555 | 1/1985 | European Pat. Off. . |
| 214779 | 3/1987 | European Pat. Off. . |
| 0021679 | 2/1983 | Japan . |
| 0227879 | 12/1984 | Japan . |
| 1003950 | 9/1965 | United Kingdom . |
| 1018995 | 2/1966 | United Kingdom . |

OTHER PUBLICATIONS

Wellcome Foundation Ltd., Chemical Abstracts, vol. 107 (1987) 58,673r.
Metvosova, Arz.-Forsch., vol. 13 (1963) 1039:43.
Benesova, Arz.-Forsch., vol. 14 (1964) 100:3.
Chem. Abs., vol. 63 (1965) 16366a.
Drugs, vol. 13 (1977) 161:218.
J. Med. Chem., vol. 19, No. 7 (1976) 941:6.
J. Med. Chem., vol. 20, No. 11 (1977) 1499:501.
J. Med. Chem., vol. 21, No. 7 (1978) 633:9.

*Primary Examiner*—Richard L. Raymond
*Attorney, Agent, or Firm*—Fitzpatrick, Cella, Harper & Scinto

[57] ABSTRACT

Novel dibenz[b,e]oxepin derivatives are employed in the treatment and control of allergic conditions such as allergic asthma and also employed in the treatment of inflammation.

3 Claims, No Drawings

DIBENZ[B,E]OXEPIN DERIVATIVE AND PHARMACEUTICAL COMPOSITIONS THEREOF

BACKGROUND OF THE INVENTION

Heretofore, it has been known that 11-unsubstituted, 11-hydroxy or 11-oxodibenz[b,e]oxepin derivative is used for antiinflammatory agents [J. Med. Chem., 21, 633-639 (1978)].

Further, it is known that dibenz[b,e]oxepin derivative wherein substitutents Ra and Rb at 11-position have the following definitions, is employed in the treatment and control of allergic conditions (U.S. Pat. No. 4,282,365).

Ra: H, OH, lower alkoxy, lower alkylthio, lower alkyl-sulfinyl, lower alkylsulfonyl, arylthio, NH₂, NHCHO or imidazolyl;

Rb: H or lower alkyl; or Ra and Rb taken together are =O, =CH—Rc wherein Rc is H or aryl.

Furthermore, it is known that 11-(4-methyl-piperazino) dibenz[b,e]oxepin derivative has an anti-asthmatic activity (U.S. Pat. No. 4,396,550, U.S. Pat. No. 4,465,835, EP-A-38564).

It is also known that dibenz[b,e]oxepin derivative having the following formula:

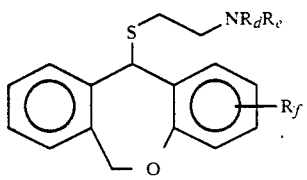

wherein Rd and Re are lower alkyl and Rf is lower alkyl or halogen, has an antiasthmatic activity (EP-A-85870).

Dibenz[b,e]oxepin derivative having an antiallergic activity and having the following structural formula:

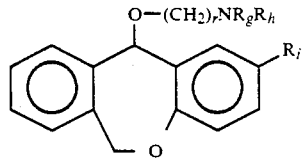

wherein Rg and Rh are alkyl, r is 2 or 3 and Ri is alkyl or halogen is known (JP-A-227879/84).

Dibenz[b,e]oxepin derivative having an antiallergic activity and having the following structural

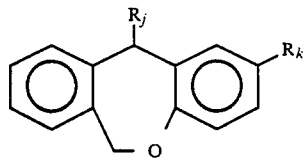

wherein Rj is 4-alkylpiperazino, 3-quinuclidylamino or —Xa—(CH₂)hd s—NR/Rₘ wherein Xₐ is —NH—, —S— or —O—, s is 2 or 3 and R/ and Rₘ are alkyl, and Rₖ is CN, 5-tetrazolyl, CONH₂ or CO₂Rₙ wherein Rₙ is H, alkyl or 1-(ethoxycarbonyloxy)ethyl is known (EP-A-130555).

Doxepin having an antidepressant activity and having the following structural formula is known [Drugs, 13, 161 (1977)].

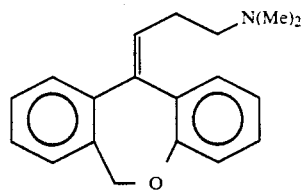

Dothiepin having an antidepressant activity and having the following structural formula is known [Arz.-Forsch., 13 1039 (1963); ibid., 14 100 (1964)].

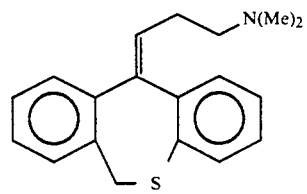

As the compound having both an antiallergic activity and an antiinflammatory activity, steroids are known.

It is always desired that a novel compound having an antiallergic activity or an antiinflammatory activity be developed.

SUMMARY OF THE INVENTION

The present invention relates to a dibenz[b,e]oxepin derivative represented by the formula (I):

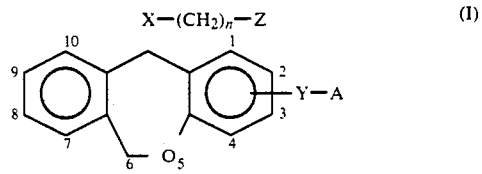

Wherein A represents a hydroxymethyl, a lower alkoxymethyl, a triphenylmethyloxymethyl, a lower alkanoyloxymethyl, a lower alkanoyl, a carboxy, a lower alkoxy carbonyl, a triphenylmethyloxycarbonyl, —CONR₁R₂ (wherein R₁ and R₂ are the same or different and represent hydrogen atom or lower alkyl) 4,4-dimethyl-2-oxazoline-2-yl group or —CONHOH; Y represents —(CH₂)ₘ—, —CHR₃—(CH₂)m— or —CR₄=CR₅—(CH₂)hd m— which is substituent at 2— or 3-position of the mother nucleus (wherein R₃ represents a lower alkyl, R₄ and R₅ are the same or different and represent a hydrogen atom or a lower alkyl, m is 0, 1, 2, 3 or 4, and the left side of the group of Y mentioned above is bound to benzen nucleus); X represents =N—, =CH— or —CH₂—; n is 0, 1, 2, 3 or 4; Z represents 4-methylpiperazino, 4-methylhomopiperazino, piperidino, pyrrolidino, thiomorpholino, morpholino, or —NR₆R₇ (wherein R₆ and R₇ are the same or different and represent a hydrogen atom or a lower alkyl); and === means a single bond or double bond [hereinafter referred to as Compound (I) and Compounds with other formula numbers are hereinafter likewise referred to], and a pharmaceutically acceptable salt thereof. The present invention further pertains to a pharmaceutical composition containing an effective amount of Compound (I) or a pharmaceutically acceptable salt thereof as an active ingredient, and a carrier or an excipient.

The present Compound (I) is useful for treatment of allergic conditions and inflammation.

DETAILED DESCRIPTION OF THE INVENTION

In the definition of each group of formula (I), the lower alkyl group includes straight or branched chain alkyl groups having 1 to 6 carbon atoms, for example, methyl, ethyl, n-propyl, iso-propyl, n-butyl, etc. In the definition of the group A, lower alkyl moiety of lower alkoxymethyl group and lower alkoxycarbonyl group has the same meaning as previously defined.

The lower alkoxymethyl group includes methoxymethyl, ethoxymethyl, n-propoxymethyl, isopropoxy, etc. and the lower alkoxycarbonyl group includes methoxycarbonyl, ethoxycarbonyl, etc.

In the definition of the group A, the lower alkyl moiety of lower alkanoyl group and lower alkanoyloxymethyl group has the same meaning as previously defined.

The lower alkanoyl group includes formyl, acetyl, etc. and the lower alkanoyloxymethyl group includes formyloxymethyl, acetyloxymethyl, etc.

The pharmaceutically acceptable salt of Compound (I) includes pharmaceutically acceptable acid addition salt, metal salt, ammonium salt, organic amine addition salt, amino acid addition salt, etc.

The pharmaceutically acceptable acid addition salt of Compound (I) includes inorganic acid salts such as hydrochloride, sulfate, phosphate, etc., and organic acid salts such as acetate, maleate, fumarate, tartrate, citrate, etc. The pharmaceutically acceptable metal salt includes alkalimetal salts such as sodium salt, potassium salt, etc., alkaline earch metal salts such as magnesium salt, calcium salt, etc., and alminium salt, zinc salt, etc. The pharmaceutically acceptable organic amine addition salt includes addition salt of morpholine and piperidine and the pharmaceutically acceptable amino acid addition salt includes addition salt of lysine, glysine, phenylalanine, etc.

Compound (I) is prepared by using a compound represented by the formula (II):

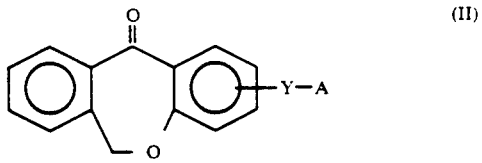

(II)

wherein Y and A have the same meanings as previously defined or a compound represented by the formula (III):

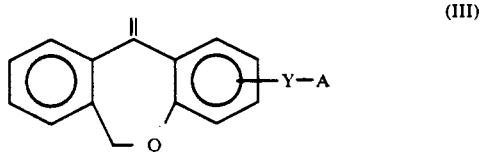

(III)

wherein Y and A have the same meanings as previously defined as the starting compound. Compound (II) is disclosed in J. Med. Chem., 19, 941 (1976), ibid., 20, 1499 (1977) and JP-A-21679/83.

Compound (III) wherein —Y—A is —COOH is disclosed in JP-A-21679/83 and the other Compounds (III) can be prepared according to the method described in the publication though they do not occur in the publication.

The process for preparing Compound (I) is explained, depending on the kind of the group X.

Process A

Synthesis of Compound (I) wherein X is =CH— (Part 1)

The carboxy group of Compound (IIa) is protected according to the following reaction scheme.

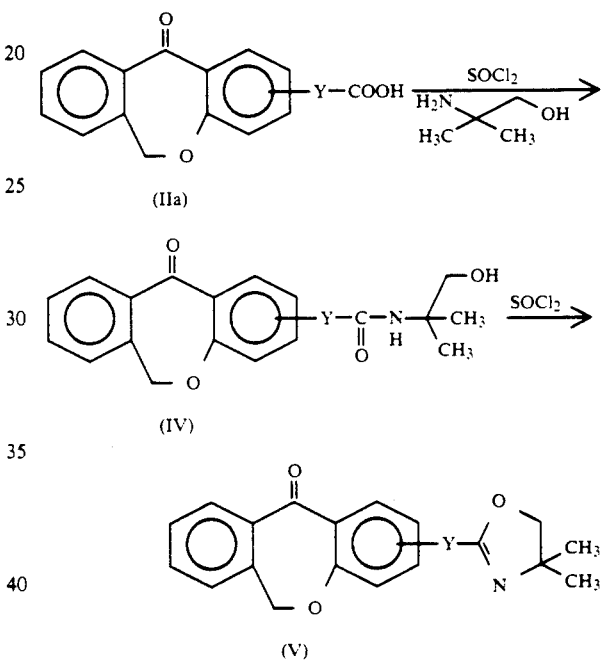

In the formulae, Y has the same meaning as previously defined, and Compound (IIa) is included in Compound (II) (compounds with an alphabet suffix following formula number are likewise included in compounds with common formula No.).

Compound (IIa) is reacted with 1 to 5 equivalents of thionyl chloride and 1 to 5 equivalents of 2-amino-2-methyl-1-propanol on the basis of Compound (IIa) in an inert solvent such as methylene chloride, if necessary in the presence of a base such as triethylamine at a temperature of from 0° C. to room temperature for 1-24 hours to form Compound (IV). Compound (IV) can also be obtained by reacting Compound (IIa) with thionyl chloride in advance and then with 2-amino-2-methyl-1-propanol.

Compound (IV) is reacted with 1-5 equivalents of thionyl chloride in an inert solvent such as methylene chloride, toluene and benzene at a temperature of from 0° C. to room temperature for 1-24 hours to form Compound (V).

Compounds (Ia) and (Ib) can be prepared from Compound (V) according to the following reaction scheme.

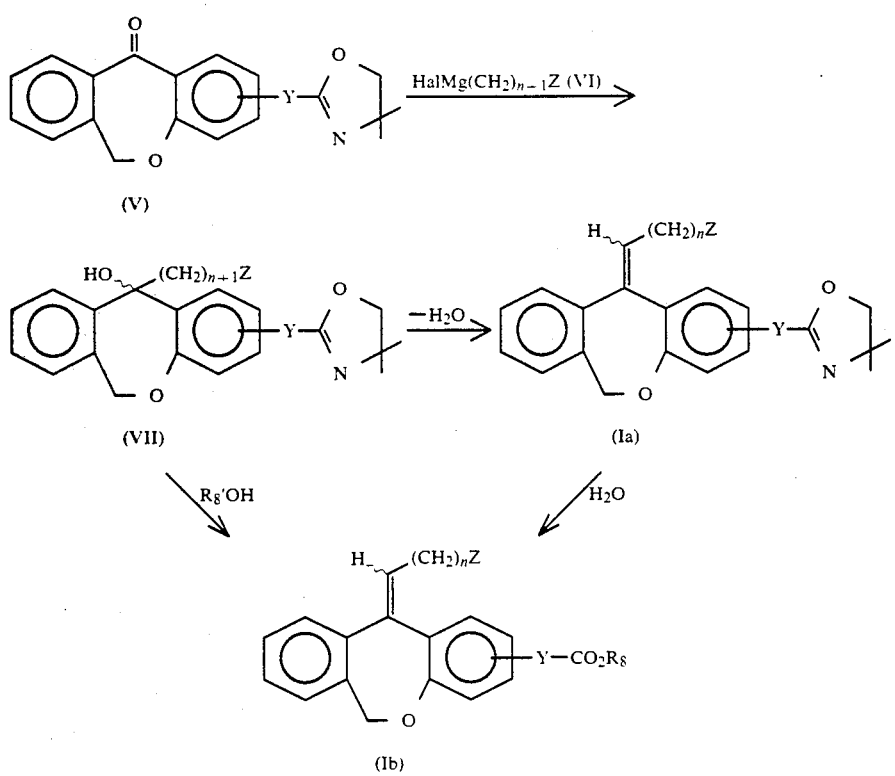

In the formulae, Y, Z, and n have the same meanings as previously defined. $R_8$ is hydrogen or a lower alkyl group, $R'_8$ is a lower alkyl group and Hal is halogen.

As used herein, the term lower alkyl has the same meaning as that of lower alkyl in each group of formula (I). Halogen includes chlorine, bromine and iodine. Compound (V) is reacted with 1-5 equivalents of Compound (VI) in an inert solvent such as tetrahydrofuran and diethyl ether under atmosphere of an inert gas such as nitrogen and argon to form Compound (VII). The reaction is carried out at a temperature of from 0° C. to room temperature and is usually completed in 1-24 hours.

Compound (VII) is reacted with 1-5 equivalents of thionyl chloride or phosphoryl chloride in an inert solvent such as methylene chloride in the presence of a base such as pyridine to form Compound (Ia). The reaction is carried out at a temperature of from 0° C. to room temperature and is completed in 1-24 hours.

Compound (Ia) is incubated in an alcohol containing water, such as aqueous methanol solution, in the presence of an appropriate acidic catalyst such as p-toluenesulfonic acid at a temperature of from room temperature to the boiling point of the solvent to form Compound (Ib) wherein $R_8$ is H. The reaction is completed in 1-24 hours.

Compound (VII) is incubated in a alcohol of $R_8'OH$ in the presence of an appropriate acidic catalyst such as p-toluenesulfonic acid at a temperature of from room temperature to the boiling point of the solvent to form Compound (Ib) wherein $R_8$ is a lower alkyl. The reaction is completed in 1-24 hours.

Process B

Synthesis of Compound (I) wherein X is =CH— (Part 2)

The carboxy group of a compound represented by the formula (IIa) can be converted to a lower alkoxymethyl group or a trityloxymethyl group according to the following reaction scheme.

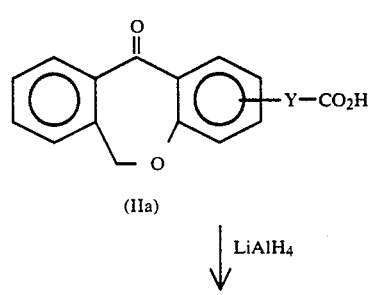

-continued

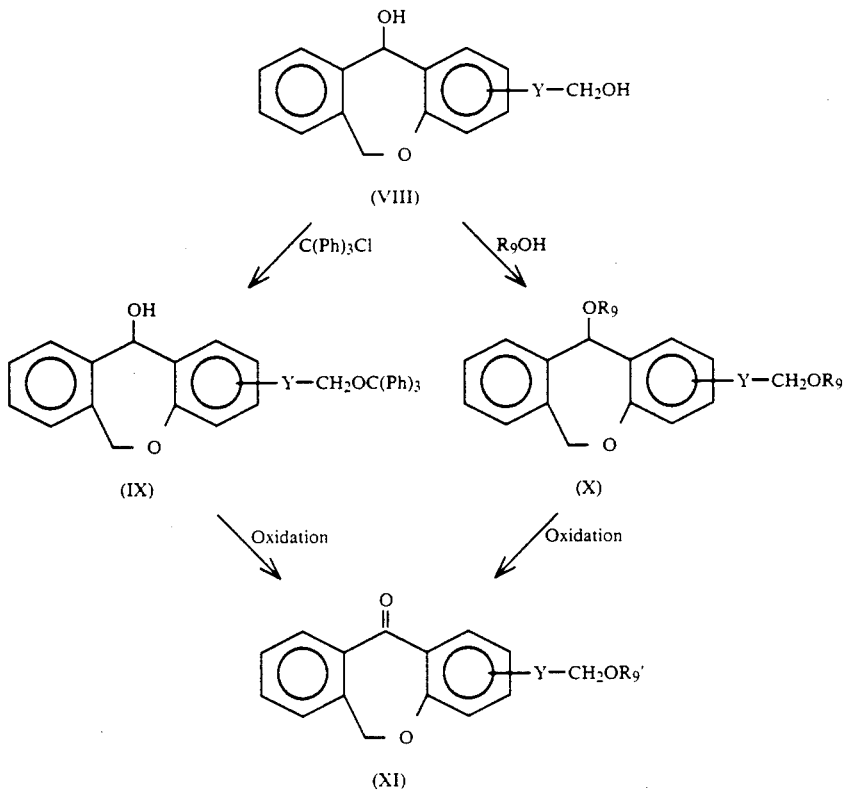

In the formulae, Y has the same meaning as previously defined, $R_9$ is a lower alkyl group and $R_9'$ is a trityl group or a lower alkyl group. The term lower alkyl has the same meaning as that of lower alkyl in each group in formula (I).

Compound (IIa) is reduced with 1-5 equivalents of lithium aluminium hydride in tetrahydrofuran at a temperature of from 0° C. to room temperature for 1-24 hours to form Compound (VIII).

Compound (VIII) is reacted with 1-5 equivalents of trityl chloride in pyridine at a temperature of from room temperature to 100° C. for 1-24 hours to form Compound (IX).

Compound (IX) is oxidized with 1-5 equivalents of an appropriate oxidizing agent such as potassium permanganate and pyridinium chlorochromate in an inert solvent such as methylene chloride and acetone to form Compound (XI) wherein $R_9'$ is trityl. The reaction is carried out at a temperature of from 0° C. to the boiling point of the solvent and is completed in 1-24 hours.

Compound (VIII) is incubated in an alcohol of $R_9OH$ in the presence of an appropriate acidic catalyst such as sulfuric acid at a temperature of from room temperature to the boiling point of the solvent to form Compound (X). The reaction is usually completed in 1-24 hours.

Compound (X) is oxidized with 1-5 equivalents of an appropriate oxidizing agent such as Jones reagent in an inert solvent such as acetone to form Compound (XI) wherein $R_9'$ is a lower alkyl. The reaction is carried out at a temperature of from 0° C. to the boiling point of the solvent and is usually completed in 1-24 hours.

The compounds represented by the formulae (Ic) and (Id) and if desired, the compound represented by the formula (Ie) can be synthesized from Compound (XI) according to the following reaction scheme.

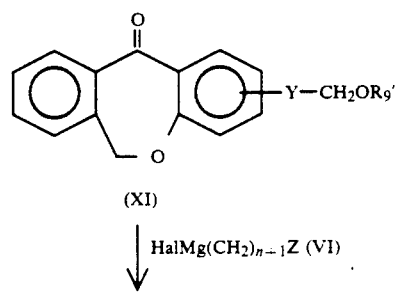

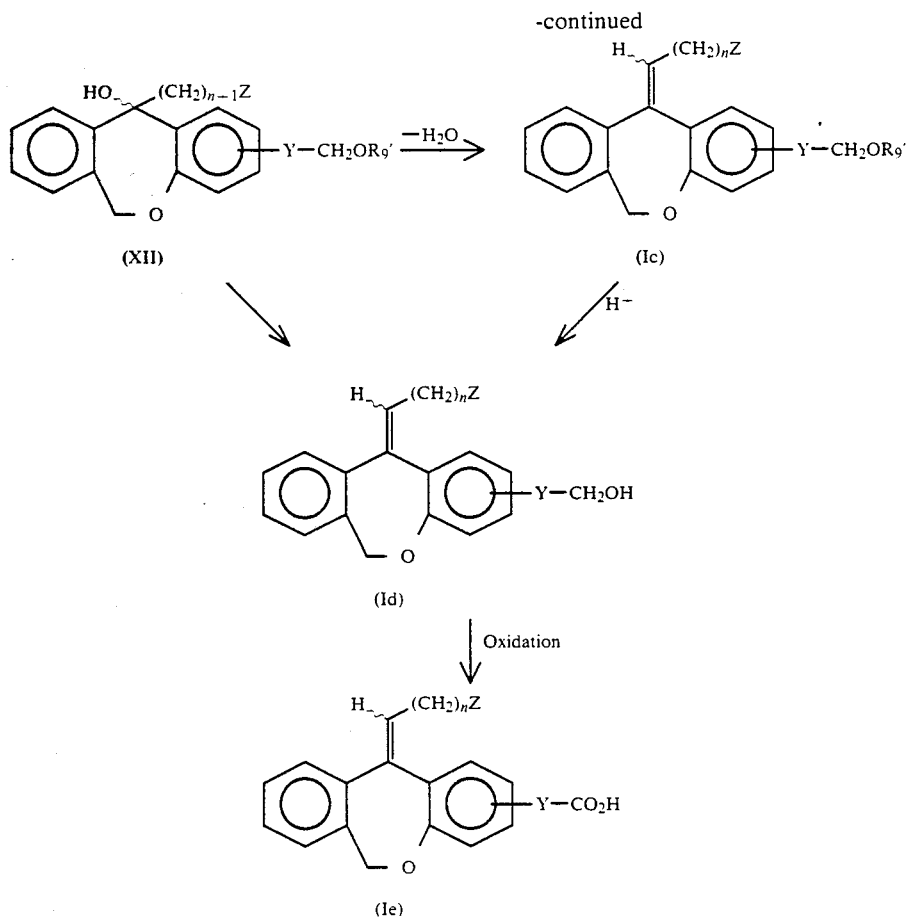

In the formulae, Y, Z, R₉', n and Hal have the same meanings as previously defined.

Compound (XI) is reacted with Compound (VI) which is Grignard reagent according to the same manner as in the reaction step from Compound (V) to Compound (VII) in Process A to form Compound (XII).

Compound (XII) is subjected to reaction according to the same manner as in the reaction step from Compound (VII) to Compound (Ia) in Process A to form Compound (Ic).

Compound (Ic) is incubated in a solvent containing water such as aqueous dioxane in the presence of an appropriate acidic catalyst such as p-toluenesulfonic acid at a temperature of from room temperature to the boiling point of the solvent to form Compound (Id). The reaction is usually completed in 1-24 hours.

Compound (Id) can also be obtained in one step by incubating Compound (XII) in a solvent containing water such as aqueous dioxane in the presence of an appropriate acidic catalyst such as sulfonic acid at a temperature of from room temperature to the boiling point of the solvent. The reaction is usually completed in 1-24 hours.

If desired, Compound (Id) is oxidized with 1-5 equivalents of an appropriate oxidizing agent such as Jones reagent in an inert solvent such as acetone to form Compound (Ie). The reaction is carried out at a temperature of from 0° C. to the boiling point of the solvent and is usually completed in 1-24 hours.

Process C

Synthesis of Compound (I) wherein X is =CH— (Part 3)

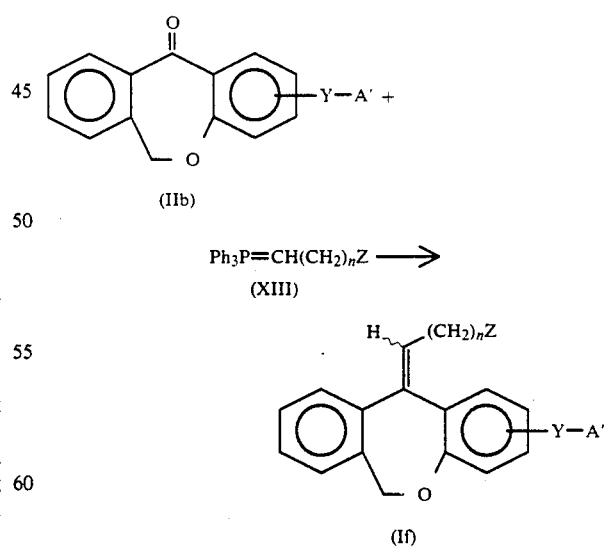

In the formulae, Y, Z, and n have the same meanings as previously defined. A' represents the groups falling within the definition of A but lower alkanoyl group.

Compound (IIb) is reacted with 1-5 equivalents of Compound (XIII) in an inert solvent such as tetrahydrofuran under atmosphere of an inert gas such as nitrogen and argon at a temperature of from 0° C. to room temperature for 1-24 hours to form Compound (If).

Compound (XIII) which is ylide, can be prepared according to the method described in C.A. 63 16366a (1965).

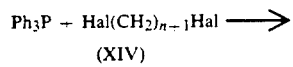
(XIV)

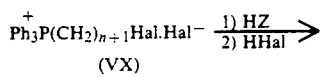
(VX)

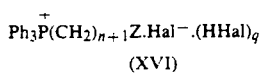
(XVI)

In the formulae, Hal, n and Z have the same meanings as previously defined and q is 1 or 2.

Compound (XIV) is reacted with an equivalent of triphenylphosphine in toluene at reflux of the solvent for 1-24 hours to form Compound (XV).

Compound (XV) is reacted with 1-5 equivalents of HZ in ethanol ar reflux of the solvent for 1-24 hours and excess HZ is distilled away under reduced pressure. After the addition of 1-5 equivalents of HHal on the basis of Compound (XV), the mixture is incubated at a temperature of from 0° C. to the boiling point of the solvent for 1-24 hours to form Compound (XVI) which is Wittig reagent.

Compound (XVI) is treated with 1-2 equivalents of an appropriate base such as n-butyl lithium in an inert solvent such as tetrahydrofuran under atmosphere of an inert gas such as nitrogen and argon to form ylide (XIII). The reaction is carried out at −78° C. to room temperature and is usually completed in 1-24 hours.

Process D

Synthesis of Compound (I) wherein X is =CH— (Part 4)

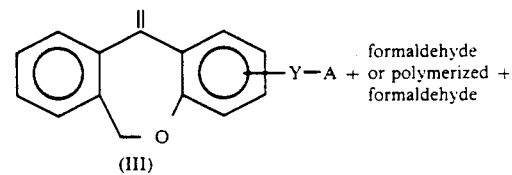

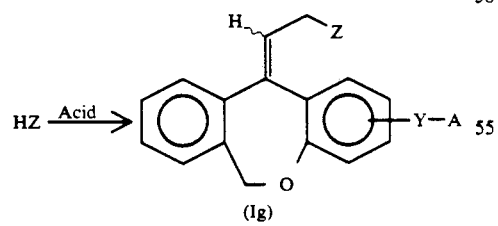

In the formulae, Y, Z and A have the same meanings as previously defined.

The process is known as Prince reaction [New Experimental Chemical Course (Maruzen), Vol. 14, Synthesis and Reaction of Organic Compound III, page 1375 (1977)].

Compound (III), 1 to 5 equivalents of formaldehyde and 1 to 5 equivalents of HZ are subjected to reaction in an inert solvent such as tetrachloroethane in the presence of an acid or reaction in an acid as such serving as a solvent under atmosphere of an inert gas such as nitrogen and argon to yield Compound (Ig).

The formaldehyde or polymerized formaldehyde includes p-formaldehyde, trioxane, etc. The acid includes acetic acid, trichloroacetic acid, trifluoroacetic acid, etc. The reaction is carried out at a temperature of from room temperature to the boiling point of the solvent and is completed in 1-24 hours.

Compound (III) which is the starting material can be prepared according to the process described in JP-A-21679/83, as shown below.

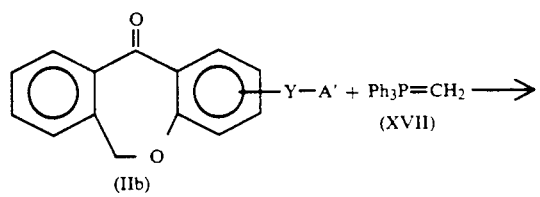
(IIb)

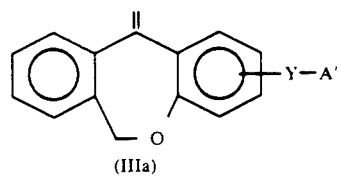
(IIIa)

That is, Compound (IIb), 1 to 5 equivalents of methyltriphenylphosphonium bromide and 1 to 5 equivalents of n-butyl lithium on the basis of Compound (IIb) are subjected to reaction in an inert solvent at from −78° C. to room temperature for 1 to 5 hours to yield ylide (XVII) which is reacted with an equivalents of Compound (IIb) in an inert solvent at from −78° C. to room temperature under atmosphere of an inert gas for 1 to 24 hours to yield Compound (IIIa).

The inert gas includes nitrogen, argon, etc. and the inert solvent includes tetrahydrofuran. etc.

The group A' in Compound (IIIa) can easily be converted to a lower alkanoyl group as is stated in Process I and therefore, Compound (III) can easily be prepared.

Process E

Synthesis of Compound (I) wherein X is=N—

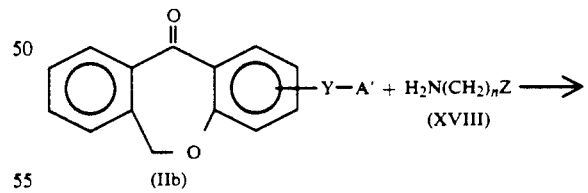
(IIb)

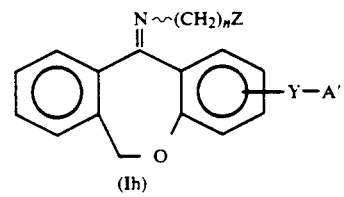
(Ih)

Compound (IIb) and 1 to 10 equivalents of Compound (XVIII) are subjected to reaction in an inert solvent such as benzene in the presence of 1 to 10 equivalents of titanium tetrachloride at from 0° C. to the boiling point of the solvent under atmosphere of an inert gas such as nitrogen and argon for 1 to 48 hours to yield Compound (Ih).

Process F

Synthesis of Compound (I) wherein X is —CH$_2$— (Part 1)

tion in an appropriate base such as pyridine at from 0° C. to room temperature to yield Compound (XX).

Compound (XX) and 1 to 5 equivalents of Compound (VI) are subjected to reaction in the same manner as in the reaction step from Compound (V) to Compound (VII) in Process A to yield Compound (Ii).

Compound (Ii) is subjected to reaction in the same

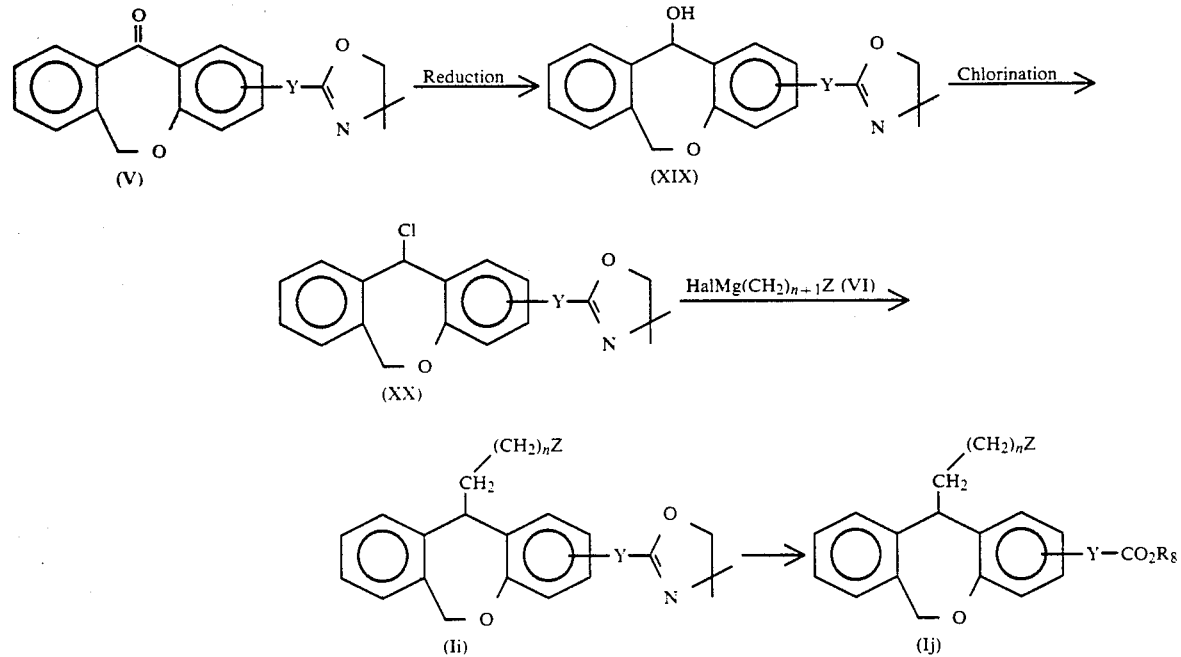

In the formulae, Y, Z, n, R$_8$ and Hal have the same meanings as previously defined.

Compound (V) is reduced with 1 to 5 equivalent of lithium aluminium hydride or sodium borohydride in an inert solvent such as tetrahydrofuran and methanol at from 0° C. to room temperature for 1 to 24 hours to yield Compound (XIX).

Compound (XIX) and 1 to 5 equivalents of thionyl chloride or phosphoryl chloride are subjected to reacmanner as in the reaction step from Compound (VII) to Compound (Ib) or the reaction step from Compound (Ia) to Compound (Ib) in Process A to yield Compound (Ij).

Process G

Synthesis of Compound (I) wherein X is —CH$_2$— (Part 2)

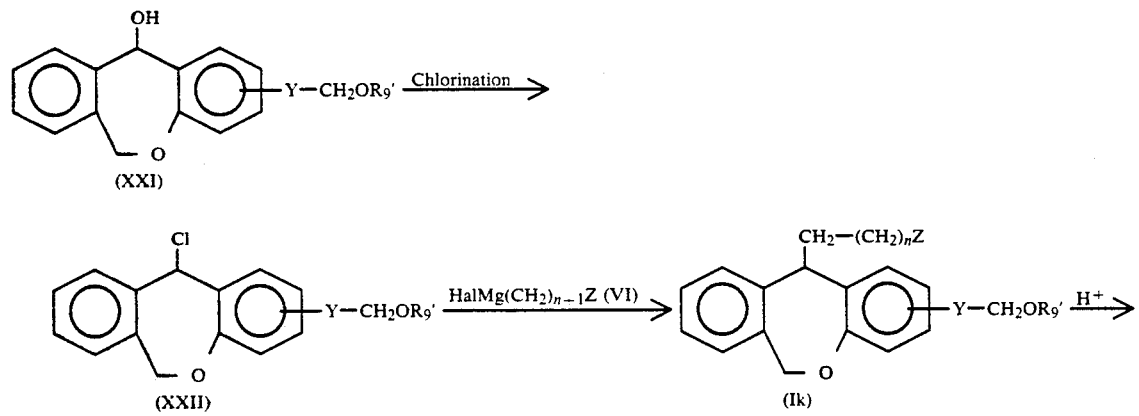

-continued

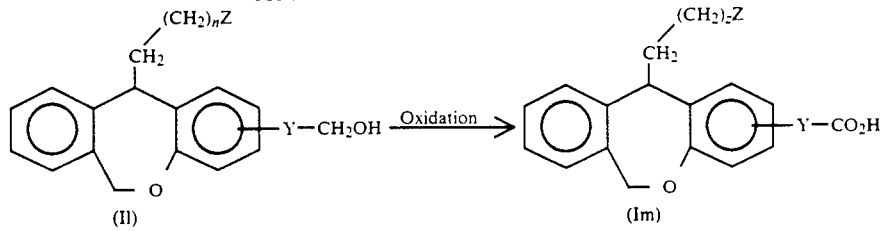

Compound (XXI) is subjected to chlorination in the same manner as in Process F to yield Compound (XXII). Compound (XXII) and Compound (VI) are subjected to reaction in the same manner as in Process F to yield Compound (Ik). Compound (Ik) is treated in the same manner as in Process B to form Compound (Il).

Compound (Il) is further treated to form Compound (Im).

Compound (IX) is included in the definition of the starting material (XXI).

Compound (XI) is reduced with 1 to 5 equivalents of lithium alminium hydride or sodium borohydride in an inert solvent such as tetrahydrofuran and methanol at from 0° C. to room temperature for 1 to 24 hours to yield Compound (XXI).

Process H

Synthesis of Compound (I) wherein X is —CH$_2$— (Part 3)

Compound (I) wherein X is —CH$_2$— can also be prepared by subjecting Compounds (Ia)–(Ig) obtained by the Processes A–D to reduction such as hydrogenation using paradium-carbon as catalyst.

The intermediates and the desired compounds in each of the processes described above can be purified and isolated by a purification method which is usually used in the field of organic chemical synthesis, such as filtration, extraction with organic solvent such as ethyl acetate and methylene chloride, drying, concentration, recrystallization, column chromatography, etc.

Out of Compounds (Ia)–(Ih) obtained in each of the processes described above, with regard to stereochemistry at 11-position of dibenz[b,e]oxepin, Compounds (Ia), (Ib), (Ic), (Id), (Ig) and (Ih) are apt to be formed as a trans-form and Compound (I$f$) is apt to be formed as a cis-form, with high frequency compared with the other form.

When Compound (I) except Compounds (Ii)–(Im) is produced as a cis-trans mixture, Compound (I) is separated and purified by an appropriate method which is usually used in the field of organic chemical synthesis, such as column chromatography, recrystallization, etc.

If desired, cis-form can be converted to trans-form. For example, cis-form is added to an acetic acid and the mixture is heated at reflux in the presence of an appropriate catalyst such as p-toluenesulfonic acid for 1–24 hours to form trans-form.

With regard to the denotation of cis-form (or cin-form) and trans form (or anti-form) of Compound (I), Compound (I) wherein the substituent bound to the double bond is on the same side as oxygen of oxepin, is cis-form (or cin-form) and Compound (I) wherein the substituent is on the opposite side is trans-form (or anti-form).

Further, if cis- or trans-form is denoted according to E-Z expression, cis-form (or cin-form) is Z-form and trans-form (or anti-form) is E-form.

For example, the compound represented by the following formula is cis-form (or cin-form or Z-form).

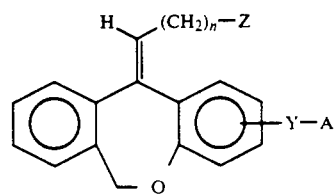

Table 1 shows examples of Compound (I) or pharmaceutically acceptable salts thereof and Table 2 shows the structural formula thereof.

Table 3 shows characteristic signals in NMR and Table 4 shows retention time in HPLC.

TABLE 1

| Compound No. | Compound (I) |
|---|---|
| 1 | Methyl cis-11-(3-dimethylaminopropylidene)-6,11-dihydrodibenz[b,e]oxepin-2-carboxylate |
|  | Methyl trans-11-(3-dimethylaminopropylidene)-6,11-dihydrodibenz[b,e]oxepin-2-carboxylate |
| 2 | Ethyl cis-11-(3-dimethylaminopropylidene)-6,11-dihydrodibenz[b,e]oxepin-2-carboxylate |
|  | Ethyl trans-11-(3-dimethylaminopropylidene)-6,11-dihydrodibenz[b,e]oxepin-2-carboxylate |
| 3 | Cis-11-(3-dimethylaminopropylidene)-6,11-dihydrodibenz[b,e]oxepin-2-carboxylic acid |
|  | Trans-11-(3-dimethylaminopropylidene)-6,11-dihydrodibenz[b,e]oxepin-2-carboxylic acid |
| 4 | Methyl cis-11-(3-diethylaminopropylidene)-6,11-dihydrodibenz[b,e]oxepin-2-carboxylate |
|  | Methyl trans-11-(3-diethylaminopropylidene)-6,11-dihydrodibenz[b,e]oxepin-2-carboxylate |
| 5 | Cis-11-(3-diethylaminopropylidene)-6,11-dihydrodibenz[b,e]oxepin-2-carboxylic acid |
|  | Trans-11-(3-diethylaminopropylidene)-6,11-dihydrodibenz[b,e]oxepin-2-carboxylic acid |
| 6 | Methyl cis-11-(3-pyrrolidinopropylidene)-6,11-dihydrodibenz[b,e]oxepin-2-carboxylate |
|  | Methyl trans-11-(3-pyrrolidinopropylidene)-6,11-dihydrodibenz[b,e]oxepin-2-carboxylate |
| 7 | Cis-11-(3-pyrrolidinopropylidene)-6,11-dihydrodibenz[b,e]oxepin-2-carboxylic acid |
|  | Trans-11-(3-pyrrolidinopropylidene)-6,11-dihydrodibenz[b,e]oxepin-2-carboxylic acid |
| 8 | Methyl cis-11-(4-dimethylaminobutylidene)-6,11-dihydrodibenz[b,e]oxepin-2-carboxylate |
|  | Methyl trans-11-(4-dimethylaminobutylidene)-6,11-dihydrodibenz[b,e]oxepin-2-carboxylate |
| 9 | Cis-11-(4-dimethylaminobutylidene)-6,11-dihydrodibenz[b,e]oxepin-2-carboxylic acid |
|  | Trans-11-(4-dimethylaminobutylidene)-6,11-dihydrodibenz[b,e]oxepin-2-carboxylic acid |
| 10 | Methyl cis-11-[2-(4-methylpiperazino)-ethylidene]-6,11-dihydrodibenz[b,e]oxepin-2-carboxylate |
|  | Methyl trans-11-[2-(4-methylpiperazino)-ethylidene]-6,11-dihydrodibenz[b,e]oxepin-2-carboxylate |

TABLE 1-continued

| Compound No. | Compound (I) |
|---|---|
| 11 | Cis-11-[2-(4-methylpiperazino)ethylidene]-6,11-dihydrodibenz[b,e]oxepin-2-carboxylic acid<br>Trans-11-[2-(4-methylpiperazino)ethylidene]-6,11-dihydrodibenz[b,e]oxepin-2-carboxylic acid |
| 12 | Methyl cis-11-(2-morpholinoethylidene)-6,11-dihydrodibenz[b,e]oxepin-2-carboxylate<br>Methyl trans-11-(2-morpholinoethylidene)-6,11-dihydrodibenz[b,e]oxepin-2-carboxylate |
| 13 | Cis-11-(2-morpholinoethylidene)-6,11-dihydrodibenz[b,e]oxepin-2-carboxylic acid<br>Trans-11-(2-morpholinoethylidene)-6,11-dihydrodibenz[b,e]oxepin-2-carboxylic acid |
| 14 | Methyl cis-11-(2-thiomorpholinoethylidene)-6,11-dihydrodibenz[b,e]oxepin-2-carboxylate<br>Methyl trans-11-(2-thiomorpholinoethylidene)-6,11-dihydrodibenz[b,e]oxepin-2-carboxylate |
| 15 | Cis-11-(2-thiomorpholinoethylidene)-6,11-dihydrodibenz[b,e]oxepin-2-carboxylic acid<br>Trans-11-(2-thiomorpholinoethylidene)-6,11-dihydrodibenz[b,e]oxepin-2-carboxylic acid |
| 16 | Methyl cis-11-(2-pyrrolidinoethylidene)-6,11-dihydrodibenz[b,e]oxepin-2-carboxylate<br>Methyl trans-11-(2-pyrrolidinoethylidene)-6,11-dihydrodibenz[b,e]oxepin-2-carboxylate |
| 17 | Methyl cis-11-(2-piperidinoethylidene)-6,11-dihydrodibenz[b,e]oxepin-2-carboxylate<br>Methyl trans-11-(2-piperidinoethylidene)-6,11-dihydrodibenz[b,e]oxepin-2-carboxylate |
| 18 | Methyl cis-11-(3-dimethylaminopropylidene)-6,11-dihydrodibenz[b,e]oxepin-2-acetate<br>Methyl trans-11-(3-dimethylaminopropylidene)-6,11-dihydrodibenz[b,e]oxepin-2-acetate |
| 19 | Ethyl cis-11-(3-dimethylaminopropylidene)-6,11-dihydrodibenz[b,e]oxepin-2-acetate<br>Ethyl trans-11-(3-dimethylaminopropylidene)-6,11-dihydrodibenz[b,e]oxepin-2-acetate |
| 20 | Cis-11-(3-dimethylaminopropylidene)-6,11-dihydrodibenz[b,e]oxepin-2-acetic acid<br>Trans-11-(3-dimethylaminopropylidene)-6,11-dihydrodibenz[b,e]oxepin-2-acetic acid |
| 21 | Methyl cis-11-(4-dimethylaminobutylidene)-6,11-dihydrodibenz[b,e]oxepin-2-acetate<br>Methyl trans-11-(4-dimethylaminobutylidene)-6,11-dihydrodibenz[b,e]oxepin-2-acetate |
| 22 | Cis-11-(4-dimethylaminobutylidene)-6,11-dihydrodibenz[b,e]oxepin-2-acetic acid<br>Trans-11-(4-dimethylaminobutylidene)-6,11-dihydrodibenz[b,e]oxepin-2-acetic acid |
| 23 | Methyl cis-11-(3-pyrrolidinopropylidene)-6,11-dihydrodibenz[b,e]oxepin-2-acetate<br>Methyl trans-11-(3-pyrrolidinopropylidene)-6,11-dihydrodibenz[b,e]oxepin-2-acetate |
| 24 | Cis-11-(3-pyrrolidinopropylidene)-6,11-dihydrodibenz[b,e]oxepin-2-acetic acid<br>Trans-11-(3-pyrrolidinopropylidene)-6,11-dihydrodibenz[b,e]oxepin-2-acetic acid |
| 25 | Methyl cis-11-[2-(4-methylpiperazino)-ethylidene-6,11-dihydrodibenz[b,e]oxepin-2-acetate<br>Methyl trans-11-[2-(4-methylpiperazino)-ethylidene]-6,11-dihydrodibenz[b,e]oxepin-2-acetate |
| 26 | Cis-11-[2-(4-methylpiperazino)-ethylidene-6,11-dihydrodibenz[b,e]oxepin-2-acetic acid<br>Trans-11-[2-(4-methylpiperazino)-ethylidene]-6,11-dihydrodibenz[b,e]oxepin-2-acetic acid |
| 27 | Methyl cis-3-[11-(3-dimethylaminopropylidene)-6,11-dihydrodibenz[b,e]oxepin-2-yl]-propionate<br>Methyl trans-3-[11-(3-dimethylaminopropylidene)-6,11-dihydrodibenz[b,e]oxepin-2-yl]-propionate |
| 28 | Cis-3-[11-(3-dimethylaminopropylidene)-6,11-dihydrodibenz[b,e]oxepin-2-yl]-propionic acid<br>Trans-3-[11-(3-dimethylaminopropylidene)-6,11-dihydrodibenz[b,e]oxepin-2-yl]-propionic acid |
| 29 | Methyl cis-11-(3-dimethylaminopropylidene)-6,11-dihydrodibenz[b,e]oxepin-3-acetate<br>Methyl trans-11-(3-dimethylaminopropylidene)-6,11-dihydrodibenz[b,e]oxepin-3-acetate |
| 30 | Cis-11-(3-dimethylaminopropylidene)-6,11-dihydrodibenz[b,e]oxepin-3-acetic acid<br>Trans-11-(3-dimethylaminopropylidene)-6,11-dihydrodibenz[b,e]oxepin-3-acetic acid |
| 31 | Cis-11-(3-dimethylaminopropylidene)-2-(2-hydroxyethyl)-6,11-dihydrodibenz[b,e]oxepin<br>Trans-11-(3-dimethylaminopropylidene)-2-(2-hydroxyethyl)-6,11-dihydrodibenz[b,e]oxepin |
| 32 | Cis-11-(3-dimethylaminopropylidene)-2-(2-triphenylmethyloxymethyl)-6,11-dihydrodibenz[b,e]oxepin<br>Trans-11-(3-dimethylaminopropylidene)-2-(2-triphenylmethyloxymethyl)-6,11-dihydrodibenz[b,e]oxepin |
| 33 | Cis-11-(3-dimethylaminopropylidene)-2-(3-hydroxypropyl)-6,11-dihydrodibenz[b,e]oxepin<br>Trans-11-(3-dimethylaminopropylidene)-2-(3-hydroxypropyl)-6,11-dihydrodibenz[b,e]oxepin |
| 34 | Methyl cin-11-(2-diethylaminoethyl)imino-6,11-dihydrodibenz[b,e]oxepin-2-carboxylate<br>Methyl anti-11-(2-diethylaminoethyl)imino-6,11-dihydrodibenz[b,e]oxepin-2-carboxylate |
| 35 | Cin-11-(2-diethylaminoethyl)imino-6,11-dihydrodibenz[b,e]oxepin-2-carboxylic acid<br>Anti-11-(2-diethylaminoethyl)imino-6,11-dihydrodibenz[b,e]oxepin-2-carboxylic acid |
| 36 | Methyl cin-11-(2-dimethylaminoethyl)imino-6,11-dihydrodibenz[b,e]oxepin-2-acetate<br>Methyl anti-11-(2-dimethylaminoethyl)imino-6,11-dihydrodibenz[b,e]oxepin-2-acetate |
| 37 | Cin-11-(2-dimethylaminoethyl)imino-6,11-dihydrodibenz[b,e]oxepin-2-acetic acid<br>Anti-11-(2-dimethylaminoethyl)imino-6,11-dihydrodibenz[b,e]oxepin-2-acetic acid |
| 38 | Methyl cin-11-(2-diethylaminoethyl)imino-6,11-dihydrodibenz[b,e]oxepin-2-acetate<br>Methyl anti-11-(2-diethylaminoethyl)imino-6,11-dihydrodibenz[b,e]oxepin-2-acetate |
| 39 | Cin-11-(2-diethylaminoethyl)imino-6,11-dihydrodibenz[b,e]oxepin-2-acetic acid<br>Anti-11-(2-diethylaminoethyl)imino-6,11-dihydrodibenz[b,e]oxepin-2-acetic acid |
| 40 | Methyl cin-11-(3-dimethylaminopropyl)imino-6,11-dihydrodibenz[b,e]oxepin-2-acetate<br>Methyl anti-11-(3-dimethylaminopropyl)imino-6,11-dihydrodibenz[b,e]oxepin-2-acetate |
| 41 | Cin-11-(3-dimethylaminopropyl)imino-6,11-dihydrodibenz[b,e]oxepin-2-acetic acid<br>Anti-11-(3-dimethylaminopropyl)imino-6,11-dihydrodibenz[b,e]oxepin-2-acetic acid |
| 42 | Methyl cin-3-[11-(2-diethylaminoethyl)imino-6,11-dihydrodibenz[b,e]oxepin-2-yl]-propionate<br>Methyl anti-3-[11-(2-diethylaminoethyl)imino-6,11-dihydrodibenz[b,e]oxepin-2-yl]-propionate |
| 43 | Cin-[11-(2-diethylaminoethyl)imino-6,11-dihydrodibenz[b,e]oxepin-2-yl]-propionic acid<br>Anti-[11-(2-diethylaminoethyl)imino-6,11-dihydrodibenz[b,e]oxepin-2-yl]-propionic acid |
| 44 | Methyl cin-2-[11-(2-dimethylaminoethyl)imino-6,11-dihydrodibenz[b,e]oxepin-2-yl]-propionate<br>Methyl anti-2-[11-(2-dimethylaminoethyl)imino-6,11-dihydrodibenz[b,e]oxepin-2-yl]-propionate |
| 45 | Cin-2-[11-(2-dimethylaminoethyl)imino-6,11-dihydrodibenz[b,e]oxepin-2-yl]-propionic acid<br>Anti-2-[11-(2-dimethylaminoethyl)imino-6,11-dihydrodibenz[b,e]oxepin-2-yl]-propionic acid |
| 46 | Methyl cin-11-(2-dimethylaminoethyl)imino-6,11-dihydrodibenz[b,e]oxepin-3-acetate<br>Methyl anti-11-(2-dimethylaminoethyl)imino-6,11-dihydrodibenz[b,e]oxepin-3-acetate |
| 47 | Cin-11-(2-dimethylaminoethyl)imino-6,11-dihydrodibenz[b,e]oxepin-3-acetic acid<br>Anti-11-(2-dimethylaminoethyl)imino-6,11-dihydrodibenz[b,e]oxepin-3-acetic acid |
| 48 | Methyl cin-11-(3-dimethylaminopropyl)imino-6,11-dihydrodibenz[b,e]oxepin-3-acetate<br>Methyl anti-11-(3-dimethylaminopropyl)imino-6,11-dihydrodibenz[b,e]oxepin-3-acetate |
| 49 | Cin-11-(3-dimethylaminopropyl)imino-6,11-dihydrodibenz[b,e]oxepin-3-acetic acid<br>Anti-11-(3-dimethylaminopropyl)imino-6,11-dihydrodibenz[b,e]oxepin-3-acetic acid |

TABLE 1-continued

| Compound No. | Compound (I) |
|---|---|
| | dihydrodibenz[b,e]oxepin-3-acetic acid |
| 50 | Methyl 11-(3-dimethylaminopropyl)-6,11-dihydrodibenz[b,e]oxepin-2-carboxylate |
| 51 | 11-(3-dimethylaminopropyl)-6,11-dihydrodibenz[b,e]oxepin-2-carboxylic acid |
| 52 | 11-(3-dimethylaminopropyl)-6,11-dihydrodibenz[b,e]oxepin-2-acetic acid |
| 53 | 11-(3-Dimethylaminopropylidene)-2-(4,4-dimethyl-2-oxazoline-2-yl)-6,11-dihydrodibenz[b,e]oxepin |
| 54 | 11-(3-Dimethylaminopropyl)-2-(4,4-dimethyl-2-oxazoline-2-yl)-6,11-dihydrodibenz[b,e]oxepin |
| 55 | Methyl cis-11-(3-morpholinopropylidene)-6,11-dihydrodibenz[b,e]oxepin-2-carboxylate<br>Methyl trans-11-(3-morpholinopropylidene)-6,11-dihydrodibenz[b,e]oxepin-2-carboxylate |
| 56 | Cis-11-(3-morpholinopropylidene)-6,11-dihydrodibenz[b,e]oxepin-2-carboxylic acid<br>Trans-11-(3-morpholinopropylidene)-6,11-dihydrodibenz[b,e]oxepin-2-carboxylic acid |
| 57 | Methyl cis-11-(3-thiomorpholinopropylidene)-6,11-dihydrodibenz[b,e]oxepin-2-carboxylate<br>Methyl trans-11-(3-thiomorpholinopropylidene)-6,11-dihydrodibenz[b,e]oxepin-2-carboxylate |
| 58 | Cis-11-(3-thiomorpholinopropylidene)-6,11-dihydrodibenz[b,e]oxepin-2-carboxylic acid<br>Trans-11-(3-thiomorpholinopropylidene)-6,11-dihydrodibenz[b,e]oxepin-2-carboxylic acid |
| 59 | Methyl trans-3-[cis-11-(3-dimethylaminopropylidene)-6,11-dihydrodibenz[b,e]oxepin-2-yl]-acrylate<br>Methyl trans-3-[trans-11-(3-dimethylaminopropylidene)-6,11-dihydrodibenz[b,e]oxepin-2-yl]-acrylate |
| 60 | Trans-3-[cis-11-(3-dimethylaminopropylidene)-6,11-dihydrodibenz[b,e]oxepin-2-yl]-acrylic acid<br>Trans-3-[trans-11-(3-dimethylaminopropylidene)-6,11-dihydrodibenz[b,e]oxepin-2-yl]-acrylic acid |
| 61 | Methyl cis-11-(3-methylaminopropylidene)-6,11-dihydrodibenz[b,e]oxepin-2-acetate<br>Methyl trans-11-(3-methylaminopropylidene)-6,11-dihydrodibenz[b,e]oxepin-2-acetate |
| 62 | Cis-11-(3-methylaminopropylidene)-6,11-dihydrodibenz[b,e]oxepin-2-acetic acid<br>Trans-11-(3-methylaminopropylidene)-6,11-dihydrodibenz[b,e]oxepin-2-acetic acid |
| 63 | Methyl cis-11-(3-aminopropylidene)-6,11-dihydrodibenz[b,e]oxepin-2-acetate<br>Methyl trans-11-(3-aminopropylidene)-6,11-dihydrodibenz[b,e]oxepin-2-acetate |
| 64 | Cis-11-(3-aminopropylidene)-6,11-dihydrodibenz[b,e]oxepin-2-acetic acid<br>Methyl trans-11-(3-aminopropylidene)-6,11-dihydrodibenz[b,e]oxepin-2-acetic acid |
| 3' | ½ Fumarate · 1/5 hydrate of Compound 3 (trans form 99%) |
| 5' | Fumarate · ½ hydrate of Compound 5 (cis form 99%) |
| 7' | Fumarate · 1 hydrate of Compound 7 (cis form 70%) |
| 11' | 2 Fumarate · ½ hydrate of Compound 11 (trans form 100%) |
| 13' | ½ Fumarate · ½ hydrate of Compound 13 (trans form 93%) |
| 15' | Fumarate of Compound 15 (trans form 100%) |
| 20' | Fumarate · 3/2 hydrate of Compound 20 (trans form 95%) |
| 26' | Fumarate · ⅜ hydrate of Compound 26 (trans form 88%) |
| 28' | Fumarate · ½ hydrate of Compound 28 (trans form 63%) |
| 31' | ½ Fumarate · 1 hydrate of Compound 31 (trans form 95%) |
| 33' | Fumarate of Compound 33 (cis form 100%) |
| 35' | Sodium salt · 1 hydrate of Compound 35 (anti:cin = 1:1) |// |
| 43' | Sodium salt of Compound 43 (anti form 98%) |
| 45' | Sodium salt · 1 hydrate of Compound 45 (anti form 99%) |
| 60' | Fumarate of Compound 60 (cis form 100%) |

TABLE 2

$$X-(CH_2)_n-Z$$

[Structure: dibenzoxepin ring system with Y—A substituent and O]

Me: methyl group
Ph: phenyl group
Et: ethyl group

| Compound No. | X | —Y—A | —(CH$_2$)$_n$—Z |
|---|---|---|---|
| 1 | CH | 2-COOMe | propyl-NMe$_2$ |
| 2 | " | 2-COOEt | " |
| 3 | " | 2-COOH | " |
| 4 | " | 2-COOMe | propyl-NEt$_2$ |
| 5 | " | 2-COOH | " |
| 6 | " | 2-COOMe | propyl-pyrrolidinyl |
| 7 | " | 2-COOH | " |
| 8 | " | 2-COOMe | butyl-NMe$_2$ |
| 9 | " | 2-COOH | " |
| 10 | " | 2-COOMe | ethyl-piperazinyl-NMe |
| 11 | " | 2-COOH | " |
| 12 | " | 2-COOMe | ethyl-morpholinyl |
| 13 | " | 2-COOH | " |
| 14 | " | 2-COOMe | ethyl-thiomorpholinyl |
| 15 | " | 2-COOH | " |
| 16 | " | 2-COOMe | ethyl-pyrrolidinyl |

TABLE 2-continued

X—(CH$_2$)$_n$—Z

[structure: dibenzoxepine-type with Y—A substituent]

Me: methyl group
Ph: phenyl group
Et: ethyl group

| Compound No. | X | —Y—A | —(CH$_2$)$_n$—Z |
|---|---|---|---|
| 17 | " | 2-COOMe | [ethyl-piperidine] |
| 18 | CH | 2-CH$_2$COOMe | [propyl-NMe$_2$] |
| 19 | " | 2-CH$_2$COOEt | " |
| 20 | " | 2-CH$_2$COOH | " |
| 21 | " | 2-CH$_2$COOMe | [butyl-NMe$_2$] |
| 22 | " | 2-CH$_2$COOH | " |
| 23 | " | 2-CH$_2$COOMe | [propyl-pyrrolidine] |
| 24 | " | 2-CH$_2$COOH | " |
| 25 | " | 2-CH$_2$COOMe | [ethyl-N-piperazine-NMe] |
| 26 | " | 2-CH$_2$COOH | " |
| 27 | " | 2-CH$_2$CH$_2$COOMe | [propyl-NMe$_2$] |
| 28 | " | 2-CH$_2$CH$_2$COOH | " |
| 29 | " | 3-CH$_2$COOMe | " |
| 30 | " | 3-CH$_2$COOH | " |
| 31 | " | 2-CH$_2$CH$_2$OH | " |
| 32 | " | 2-CH$_2$CH$_2$OC(Ph)$_3$ | " |
| 33 | " | 2-CH$_2$CH$_2$CH$_2$OH | " |
| 34 | N | 2-COOMe | [propyl-NEt$_2$] |
| 35 | " | 2-COOH | " |
| 36 | " | 2-CH$_2$COOMe | [propyl-NMe$_2$] |
| 37 | " | 2-CH$_2$COOH | " |
| 38 | N | 2-CH$_2$COOMe | [propyl-NEt$_2$] |
| 39 | " | 2-CH$_2$COOH | " |
| 40 | " | 2-CH$_2$COOMe | [butyl-NMe$_2$] |
| 41 | " | 2-CH$_2$COOH | " |
| 42 | " | 2-CH$_2$CH$_2$COOMe | [propyl-NEt$_2$] |
| 43 | " | 2-CH$_2$CH$_2$COOH | " |
| 44 | " | 2-CH(CH$_3$)COOMe | [propyl-NMe$_2$] |
| 45 | " | 2-CH(CH$_3$)COOH | " |
| 46 | " | 3-CH$_2$COOMe | " |
| 47 | " | 3-CH$_2$COOH | " |
| 48 | " | 3-CH$_2$COOMe | [butyl-NMe$_2$] |
| 49 | " | 3-CH$_2$COOH | " |
| 50 | CH$_2$ | 2-COOMe | [propyl-NMe$_2$] |
| 51 | " | 2-COOH | " |
| 52 | " | 2-CH$_2$COOH | " |
| 53 | CH | 2-[oxazoline] | [propyl-NMe$_2$] |
| 54 | CH$_2$ | 2-[oxazoline] | " |
| 55 | CH | 2-COOMe | [propyl-morpholine] |
| 56 | " | 2-COOH | " |
| 57 | CH | 2-COOMe | [propyl-thiomorpholine] |
| 58 | " | 2-COOH | " |
| 59 | " | 2-CH=CH—COOMe | [propyl-NMe$_2$] |
| 60 | " | 2-CH=CH—COOH | " |
| 61 | " | 2-CH$_2$COOMe | [propyl-NHMe] |
| 62 | " | 2-CH$_2$COOH | " |
| 63 | " | 2-CH$_2$COOMe | [propyl-NH$_2$] |
| 64 | " | 2-CH$_2$COOH | " |

TABLE 3

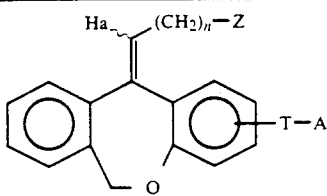

| Compound | Chemical sift of Ha proton (ppm) Cis | Trans | Measure solvent |
|---|---|---|---|
| 1 | 5.67 | 6.06 | A |
| 2 | 5.70 | 6.07 | A |
| 3 | 5.72 | 6.09 | B |
| 4 | 5.69 | 6.05 | A |
| 5 | 5.73 | — | B |
| 6 | 5.70 | 6.07 | A |
| 7 | 5.71 | 6.09 | B |
| 8 | 5.70 | 6.08 | A |
| 9 | 5.71 | 6.08 | B |
| 10 | 5.85 | 6.22 | A |
| 11 | — | 6.11 | B |
| 12 | 5.81 | 6.20 | A |
| 13 | 5.81 | 6.13 | B |
| 14 | 5.81 | 6.18 | A |
| 15 | 5.80 | 6.13 | B |
| 16 | 5.83 | 6.19 | A |
| 17 | 5.92 | 6.28 | A |
| 18 | 5.69 | 6.06 | A |
| 19 | 5.70 | 6.07 | B |
| 20 | 5.66 | 6.00 | B |
| 21 | 5.66 | 6.02 | B |
| 22 | 5.67 | 6.02 | B |
| 23 | 5.69 | 5.99 | A |
| 24 | 5.60 | 5.92 | A |
| 25 | 5.84 | 6.17 | A |
| 26 | 5.72 | 6.05 | B |
| 27 | 5.69 | 6.57 | A |
| 28 | 5.50 | 5.99 | B |
| 31 | 5.66 | 5.99 | A |
| 32 | 5.69 | 6.97 | A |
| 33 | 5.65 | — | A |
| 55 | 5.67 | 6.06 | A |
| 56 | 5.73 | 6.10 | B |
| 57 | 5.68 | 6.03 | A |
| 58 | 5.70 | 6.08 | B |
| 59 | 5.72 | — | A |
| 60 | 5.71 | — | B |
| 61 | 5.63 | — | A |
| 62 | 5.65 | — | B |
| 63 | 5.68 | — | A |
| 64 | 5.67 | — | B |

A = CDCl$_3$
B = DMSO-d$_6$

TABLE 4

| Compound | Retention time in HPLC (Minutes) Cis | Trans | Eluent |
|---|---|---|---|
| 3 | 10.33 | 8.33 | B |
| 5 | 7.19 | 6.06 | C |
| 7 | 10.83 | 8.79 | B |
| 9 | 14.26 | 11.40 | B |
| 11 | 27.06 | 21.33 | A |
| 13 | 16.59 | 13.13 | A |
| 15 | — | 14.73 | A |
| 20 | 9.93 | 7.46 | B |
| 22 | 11.10 | 8.40 | B |
| 24 | 10.50 | 8.00 | B |
| 26 | 11.20 | 8.93 | B |
| 28 | 11.60 | 9.10 | B |
| 33 | 11.06 | — | B |
| 56 | 11.34 | 8.95 | B |
| 58 | 12.41 | 7.75 | B |
| 60 | 11.29 | — | B |
| 62 | 10.77 | — | B |
| 64 | 10.65 | — | B |

| Compound | Retention time in HPLC (Minutes) Cis | Trans | Eluent |
|---|---|---|---|
| Instrument: | SHIMAZU LC-3A | | |
| Column | Yamamurakagaku YMC A-312 | | |
| | A 0.01M PIC B-8 in 54.3% MeOH | | |
| | B 0.01M PIC B-8 in 61.3% MeOH | | |
| | C 0.01M PIC B-8 in 66.0% MeOH | | |
| * PIC: | PIC reagent (Produced by Water Associates) | | |
| Pressure: | 85-95 kg/cm$^2$ | | |
| Temperature: | room temperature | | |

Compound (I) has both an antiallergic activity and antiinflammatory activity. Among Compound (I), the compound represented by the formula (I') has strong antiallergic activity and the compound represented by the formula (II') has strong antiinflammatory activity.

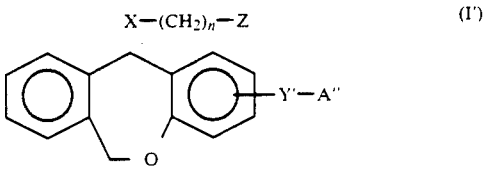

In the formula, X, n and Z are as previously defined, —Y'—A" is —Y—A when X is =CH— or —CH$_2$— and is —Y—A which is bound at 2 position of the mother nucleus when X is =N—, and Y and A are as previously defined.

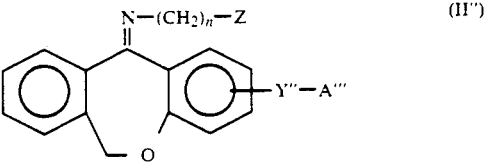

In the formula, n and Z are as previously defined; Y''' is —CH$_2$— or —CHR$_3$— substituted at 2 or 3 position of the mother nucleus wherein R$_3$ is a lower alkyl; A''' is a hydroxymethyl, a loweralkoxymethyl, a triphenylmethyloxymethyl, a lower alkanoyloxymethyl, a formyl, a carboxyl, a lower alkoxycarbonyl, a triphenylmethyloxycarbonyl, —CONR$_1$R$_2$ wherein R$_1$ and R$_2$ are the same or different and are hydrogen atom or a lower alkyl, 4,4-dimethyl-2-oxazoline-2-yl or —CONHOH.

The antiallergic activity and antiinflammatory activity of Compound (I) are described below:

Test for antiallergic activity

Antiallergic activity was investigated by a homologous PCA (passive cutaneous anaphlaxis) of rats for 48 hours, where Wistar male rats having body weights of 180 to 220 g were used for sampling of antiserum and Wistar male rats having body weights of 120 to 140 g were used for the PCA test.

A) Preparation of anti EWA rat serum

Anti-egg white albumin (EWA) rat serum was prepared according to Stotland and Share's method [Canad. J. Physiol. Pharmacol. 52, 1114 (1974)]. That is, 1 mg of EWA was mixed with 20 mg of aluminum hydroxide gel and 0.5 ml of mixed vaccine of pertussis, diphtheria and tetanus, and the mixture was subcutaneously administered in four portions into rat's footpad. After 14 days, blood was sampled from the carotid artery, and the serum was separated from the sampled blood, and preserved under freezing at $-80°$ C. The potency of the antiserumin in the homologous PCA for 48 hours was 1:32.

B) Homologous PCA test of rats for 48 hours

Groups each consisting of 3 rats were used, and 0.05 ml of anti-EWA rat serum diluted with a physiological saline solution to 8 times as much was incutaneously injected each at two positions of depilated back to make the animals passively sensitised. After 47 hours, the compound of the present invention, or its solution (physiological saline solution or CMC solution) was orally administered. One hour thereafter, 0.5 ml/100 g of 1% Evan's blue physiological saline solution containing 2 mg of the antigen EWA was administered into the tail vein, and 30 minutes thereafter, the animals were sacrificed by exsanguination. Then, the skins were stripped and the amount of leaked pigment at the blue-dyed parts was measured according to the Katayama et al method [Microbiol. Immunol. 22, 89 (1978)]. That is, the blue-dyed parts were cut out by scissors, and placed in test tubes containing 1 ml of 1N KOH and incubated at 37° C. for 24 hours. Then, 9 ml of a mixture of 0.6N phosphoric acid and acetone (5:13) was added thereto, and the mixture was shaken and centrifuged at 2,500 rpm for 10 minutes. Absorbancy of the supernatant at 620 μm was measured, and the amount of leaked pigment was quantitatively determined by the calibration curve prepared in advance. An average of measurements at the two position was made a value for one zooid, and inhibition rate for the individual zooid was calculated by the following formula:

$$\text{Inhibition rate (\%)} = \frac{\text{Average leaked amount of solvent-administered group} - \text{Leaked amount of test compound-administered group}}{\text{Average leaked amount of solvent-administered group}} \times 100$$

Cases where, the inhibition rate is 50% or higher, were regarded as positive PCA inhibition activity, and the minimum administered dosage, where a positive case was observed in at least one of three zooids was regarded as minimum effective dosage (MED). The results are shown in Table 5.

Acute Toxic Test

Groups each consisting of 3 dd, male mice having body weights of $20\pm1$ g were used, and the compound of the present invention was administered orally (po: 300 mg/kg) or intraperitoneally (ip: 100 mg/kg). Mortality 7 days after the administration was observed to obtain MLD (minimum lethal dosage). The results are shown in Table 5.

Antiinflammatory Activity Test

Antiinflammatory activity was examined according to Rat carageenin paw edema [J. Pathol. 104, 15-29 (1971)]. Groups each consisting of three Wistar male rats weighing 150 g were used. The test compound was suspended in 0.3% aqueous CMC solution and the suspension was given orally. Sixty minutes later, 0.1 ml of 0.1% carageenin was subcutaneously injected in a hind paw to form carageenin paw edema.

The volume of paw was measured before the administration and 3 hours after the administration of carageenin with plethysmometer.

The ratio of the volume 3 hours after the administration to that before the administration of carageenin was calculated and each ratio is compared with the ratio of control group (0.3% CMC was administered) to give the edema inhibiting percentage. The results are shown in Table 6.

TABLE 5

| Compound | Acute toxicity (MLD) mg/kg po | ip | Antiallergic Activity Number of positive zooids in one group of 3 zooids Dosage mg/kg 100 | 10 | 1 | 0.1 | 0.01 | 0.001 | M E D mg/kg |
|---|---|---|---|---|---|---|---|---|---|
| 3 (cis) | >300 | >100 | 3/3 | 3/3 | 3/3 | 3/3 | 0/3 | — | 0.1 |
| 3' (trans) | >300 | >100 | 3/3 | 2/3 | 1/3 | 1/3 | 0/3 | — | 0.1 |
| 5' (cis) | >300 | >100 | 3/3 | 3/3 | 3/3 | 0/3 | 0/3 | — | 1 |
| 7' (cis:trans = 7:3) | >300 | >100 | 3/3 | 2/3 | 1/3 | 0/3 | — | — | 1 |
| 9 (cis:trans = 91:9) | >300 | >100 | 3/3 | 3/3 | 2/3 | 0/3 | 0/3 | — | 1 |
| 11' (trans) | >300 | >100 | 2/3 | 1/3 | 0/3 | 0/3 | — | — | 10 |
| 13' (cis:trans = 7:93) | >300 | >100 | 3/3 | 1/3 | 0/3 | 0/3 | — | — | 10 |
| 15' (trans) | — | — | 3/3 | 0/3 | 0/3 | 0/3 | — | — | 100 |
| 20' (trans) | >300 | >100 | 3/3 | 3/3 | 3/3 | 1/3 | 0/3 | — | 0.1 |
| 20 | >300 | >100 | 2/3 | 2/3 | 3/3 | 3/3 | 0/3 | 0/3 | 0.1 |

TABLE 5-continued

| Compound | Acute toxicity (MLD) mg/kg | | Antiallergic Activity Number of positive zooids in one group of 3 zooids Dosage mg/kg | | | | | | M E D mg/kg |
|---|---|---|---|---|---|---|---|---|---|
| | po | ip | 100 | 10 | 1 | 0.1 | 0.01 | 0.001 | |
| 20 (trans) (cis) | >300 | >100 | 3/3 | 3/3 | 3/3 | 3/3 | 1/3 | 0/3 | 0.01 |
| 22 (cis:trans = 92:8) | >300 | >100 | 3/3 | 3/3 | 2/3 | 1/3 | 0/3 | — | 0.1 |
| 26' (cis:trans = 12:88) | >300 | >100 | 3/3 | 3/3 | 2/3 | 0/3 | — | — | 1 |
| 28' (cis:trans = 37:63) | >300 | >100 | 3/3 | 3/3 | 3/3 | 2/3 | 2/3 | 0/3 | 0.01 |
| 28 (cis) | >300 | >100 | 3/3 | 2/3 | 3/3 | 1/3 | 0/3 | — | 0.1 |
| 28 (trans) | >300 | >100 | 3/3 | 3/3 | 2/3 | 2/3 | 1/3 | 0/3 | 0.01 |
| 31' (trans) | >300 | >100 | 3/3 | 3/3 | 3/3 | 1/3 | 0/3 | — | 0.1 |
| 31 (trans) | >300 | >100 | 3/3 | 3/3 | 2/3 | 3/3 | 0/3 | — | 0.1 |
| 31 (cis) | 300 | >100 | — | 3/3 | 3/3 | 2/3 | 0/3 | 0/3 | 0.1 |
| 33' (cis) | NT | NT | 3/3 | 3/3 | 1/3 | 0/3 | — | — | 1 |
| 35' (cin:anti = 1:1) | 300> | 100> | 3/3 | 1/3 | 0/3 | — | — | — | 10 |
| 37 (cin:anti = 8:92) | 300> | 100> | 3/3 | 3/3 | 0/3 | — | — | — | 10 |
| 39 (cin:anti = 2:98) | 300> | 100> | 3/3 | 2/3 | 3/3 | 0/3 | — | — | 1 |
| 41 (cin:anti = 3:97) | 300> | 100> | 3/3 | 2/3 | 1/3 | 0/3 | — | — | 1 |
| 43' cin:anti mixture | 300> | 100> | 3/3 | 2/3 | 0/3 | 0/3 | — | — | 10 |
| 45' (anti) | 300> | 100> | 3/3 | 3/3 | 2/3 | 0/3 | — | — | 1 |
| 56' (cis:trans = 87:13) | >300 | >100 | 3/3 | 3/3 | 3/3 | 1/3 | 0/3 | — | 0.1 |
| 58 (cis:trans = 87:13) | >300 | >100 | 3/3 | 3/3 | 3/3 | 0/3 | — | — | 1 |
| 60' (cis) | >300 | >100 | 3/3 | 3/3 | 2/3 | 1/3 | 0/3 | — | 0.1 |

TABLE 6

| Compound No. | Carageenin paw edema inhibiting percentage (%) (Average value in one group of 3 rats, 100 mg/kg oral administration) |
|---|---|
| 37 | 51.6 |
| 39 | 50.2 |
| 41 | 38.7 |
| 45' | 63.1 |
| 47 | 46.0 |
| 49 | 24.1 |

As is evidenced in Tables 5 and 6, Compound (I) and pharmaceutically acceptable salt thereof have PCA inhibiting activity and/or carageenin paw edema inhibiting activity.

PCA inhibiting activity is believed to be on the basis of an activity inhibiting liberation of chemical mediator such as histamine from fat skin cell. Therefore, Compound (I) and pharmaceutically acceptable salts thereof are believed to be useful for treating an allergic disease such as bronchus asthma which is caused by trachea contractile activity of chemical mediator such as histamine.

On the other hand, carageenin paw edema inhibiting activity is believed to be on the basis of prostaglandin biosynthesis inhibiting activity. Thus, Compound (I) and pharmaceutically acceptable salts thereof are believed to be useful for treating an acute inflammation and rheumatism which are ascribed to excessive prostaglandin.

Compound (I) includes a compound having both antiallergic and antiinflammatory activities described above which is useful for the treatment of allergic diseases accompanied by inflammation.

In view of the pharmacological activity of Compound (I), Compound (I) can be used in various medicament forms for the administration purposes.

The present medicament composition can be prepared by uniformly mixing an effective amount of a free Compound (I) or a pharmaceutically acceptable salt thereof as an active component with a pharmaceutically acceptable carrier or excipient. The carrier can take a wide range of forms in accordance with a desirable medicament form for the administration. These medicament compositions are desirably in a unit dosage form suitable for the oral administration or injection administration. In the preparation of a composition in the oral dosage form, any useful, pharmaceutically acceptable carrier can be used. For example, an oral liquid preparation such as a suspended medicament or syrup medicament can be prepared using water; sugars such as sucrose, sorbitol, fructose, etc.; glycols such as polyethylene glycol, propylene glycol, etc.; oils such as sesame oil, olive oil, soybean oil, etc.; antiseptics such as alkyl parahydroxybenzoate, etc.; and flavors such as strawberry flavor, peppermint, etc. Powder, pills, capsules and tablets can be prepared using an excipient such as lactose, glucose, sucrose, mannitol, etc.; a disintegrator such as starch, sodium alginate, etc.; a lubricant such as magnesium stearate, talc, etc.; a binder such as polyvinyl alcohol, hydroxypropylcellulose, gelatin, etc.; a surfactant such as fatty acid esters; and a plasticizer such as glycerine, etc. Tablets and capsules are the most useful, oral unit dosage forms because of easy administration. To prepare tablets and capsules, solid carriers for medicament are used. Injection solution can be prepared using a carrier consisting of a salt solution, a glucose solution or a mixture of the salt solution and the glucose solution. The effective dosage of Compound (I) is 1 to 20 mg/kg/day for a human being, and number of administration is 3 to 4 per day.

Examples and Reference Examples are given below:

REFERENCE EXAMPLE 1

(Raw material 1) Methyl 11-oxo-6,11-dihydrodibenz[b,e]oxepin-2-carboxylate

In this example, 348.9 g of sodium salt of methyl p-hydroxybenzoate, 402.4 g of phthalide and 200 g of sodium chloride are mixed with one another and stirred at 150° C. for 6 hours. After completion of the reaction, the mixture is cooled until the temperature is brought back to room temperature, 4 l of aqueous 10% acetic acid solution is added thereto and the mixture is allowed to stand at room temperature overnight. After stirring the mixture at room temperature for 3 hours, deposited crystals are separated by filtration, and 6 l of water is added thereto. After stirring the mixture at room temperature for 30 minutes, the deposited crystals are separated by filtration. After the addition of 3 l of toluene to the crystals, the mixture is stirred at room temperature for one hour. The crystals are separated by filtration and dried over heating under reduced pressure to yield 393.9 g of 2-(4-methoxycarbonylphenoxy) methyl benzoic acid.

IR (KBr disk): 3400, 1700, 1610, 1260, 1235 cm$^{-1}$ The thus obtained 2-(4-methoxycarbonylphenoxy) methyl benzoic acid (392.7 g) is suspended in 5.0 l of methylene chloride and 266.0 g of trifluoroacetic anhydride is added thereto. After stirring the mixture at room temperature for one hour, 19.4 g of boron trifluoride-ethylether complex is added thereto and the mixture is stirred at room temperature for two hours. The reaction solution is poured into ice water. After an organic solvent layer is separated from the mixture, the organic layer is washed with diluted aqueous sodium hidroxide solution and water, dried over anhydrous magnesium sulfate and concentrated under reduced pressure to obtain 335.3 g of methyl 11-oxodibenz[b,e]oxepin-2-carboxylate as a white crystal.

Melting point and elementary analysis are shown in Table 7.

IR (KBr disk): 1710, 1650, 1610, 1250, 1010 cm$^{-1}$
NMR (CDCl$_3$, δ, ppm): 3.84(s, 3H), 5.14(s, 2H), 6.87–8.93(m, 7H)

REFERENCE EXAMPLES 2–5

(Raw material 2) 11-Oxo-6,11-dihydrodibenz[b,e]oxepin-2-acetic acid
(Raw material 3) 11-Oxo-6,11-dihydrodibenz[b,e]oxepin-3-acetic acid
(Raw material 4) 2-(11-Oxo-6,11-dihydrodibenz[b,e]oxepin-2-yl)-propionic acid
(Raw material 5) 3-(11-Oxo-6,11-dihydrodibenz[b,e]oxepin-2-yl)-propionic acid Raw materials 2–5 are produced by respectively substituting p-hydroxyphenyl acetic acid, m-hydroxyphenyl acetic acid, 2-(p-hydroxyphenyl)-propionic acid and 3-(p-hydroxyphenyl)-propionic acid for methyl p-hydroxybenzoate in Reference example 1.

Melting points and elementary analyses thereof are shown in Table 7.

REFERENCE EXAMPLE 6

(Raw material 6) Methyl 11-methylene-6,11-dihydrodibenz-[b,e]oxepin-2-carboxylate In 100 ml of tetrahydrofuran is suspended 25 g of methyltriphenylphosphonium bromide and 40 ml of 1.6 N-n-butyl lithium helium hexane solution is dropwise added thereto under a nitrogen atmosphere and ice-cooling. After stirring the mixture under ice-cooling for 30 minutes, a solution obtained by dissolving 15 g of methyl 11-oxo-6,11-dihydrodibenz[b,e]oxepin-2-carboxylate in 250 ml of tetrahydrofuran is dropwise added thereto and the mixture is stirred at room temperature for two hours. The solvent is distilled away under reduced pressure and the residue is purified by column chromatography on silica gel (eluent: hexane:ethyl acetate=3:1) to obtain 3.7 g of the desired product as a colorless oily matter.

NMR (CDCl$_3$, δ, ppm): 3.83(s, 3H), 5.15(s, 2H), 5.29 (s, 1H), 5.74(s, 1H), 6.69–8.22(m, 7H)

Melting point and elementary analysis are shown in Table 7.

REFERENCE EXAMPLE 7

(Raw material 7) Methyl 11-methylene-6,11-dihydrodibenz-[b,e]oxepin-2-acetate

The desired product is obtained by substituting 11-oxo-6,11-dihydrodibenz[b,e]oxepin-2-acetic acid for methyl 11-oxo-6,11-dihydrodibenz[b,e]oxepin-2-carboxylate in Reference example 6.

Colorless oily matter
NMR (CDCl$_3$, δ, ppm): 3.48(s, 2H), 3.61(s, 3H), 5.05 (s, 2H), 5.20(s, 1H), 5.62(s, 1H), 6.59–7.43 (m, 7H)
IR (neat, cm$^{-1}$): 2950, 1740, 1615, 1490, 1010
Melting point and elementary analysis are shown in Table 7.

REFERENCE EXAMPLE 8

(Raw material 8) 11-Methylene-6,11-dihydrodibenz[b,e]-oxepin-2-acetic acid

To a mixed solvent of 200 ml of methanol and 50 ml of 2N-aqueous sodium hydroxide solution is added 2.9 g of methyl 11-methylene-6,11-dihydrodibenz[b,e]oxepin-2-acetate (raw material 7, Reference example 7) and the mixture is heated at reflux for two hours. After allowing the mixture to stand for cooling, the mixture is concentrated under reduced pressure, and the pH of the mixture is adjusted to 1.0 with aqueous 4N-hydrochloric acid solution. The mixture is extracted with 500 ml of ethyl acetate, washed with aqueous 1N-hydrochloric acid solution and saturated aqueous sodium chloride solution in order and dried over anhydrous sodium sulfate. The solvent is distilled away under reduced pressure and the resultant crude product is crystallized from hexane to obtain 2.7 g of the desired product as a white solid.

NMR (DMSO-$d_6$+$D_2O$, δ, ppm): 3.45(s, 2H), 5.02(s, 2H), 5.16(s, 1H), 5.60(s, 1H), 6.45–7.44(m, 7H)

Melting point and elementary analysis are shown in Table 7.

REFERENCE EXAMPLE 9

(Raw material 9) Methyl 11-methylene-6,11-dihydrodibenz-[b,e]oxepin-3-acetate

The desired product is obtained by substituting 11-oxo-6,11-dihydrodibenz[b,e]oxepin-3-acetic acid for methyl 11-oxo-6,11-dihydrodibenz[b,e]oxepin-2-carboxylate in Reference example 6.

REFERENCE EXAMPLE 10

(Raw material 10) 11-Methylene-6,11-dihydrodibenz[b,e]oxepin-3-acetic acid

The desired product is obtained by substituting methyl 11-methylene-6,11-dihydrodibenz[b,e]oxepin-3-acetate for methyl 11-methylene-6,11-dihydrodibenz[b,e]oxepin-2-acetate in Reference example 8.

TABLE 7

| Raw material | Melting point (°C.) | Elementary analysis (%) or mass spectrum | | |
|---|---|---|---|---|
| 1 | 128–129 | as $C_{16}H_{12}O_4$ | | |
| | | | C | H |
| | (Isopropyl ether) | Calculated | 71.63 | 4.51 |
| | | Found | 71.55 | 4.48 |
| 2 | 130–132 | as $C_{16}H_{12}O_4$ | | |
| | | | C | H |
| | (Ethyl acetate) | Calculated | 71.63 | 4.51 |
| | | Found | 71.86 | 4.55 |
| 3 | 111–114 | as $C_{16}H_{12}O_4$ | | |
| | | | C | H |
| | (Ethyl acetate) | Calculated | 71.63 | 4.51 |
| | | Found | 71.53 | 4.66 |
| 4 | Syrup | as $C_{17}H_{14}O_4$ (M + 282) | | |
| 5 | 144–145 | as $C_{17}H_{14}O_4$ | | |
| | | | C | H |
| | (Water) | Calculated | 72.33 | 5.00 |
| | | Found | 72.45 | 5.20 |
| 6 | Syrup | as $C_{17}H_{14}O_3$ (M + 266) | | |
| 7 | Syrup | as $C_{18}H_{16}O_3$ (M + 280) | | |
| 8 | 162–163 | as $C_{17}H_{14}O_3$ | | |
| | | | C | H |
| | (Water) | Calculated | 76.68 | 5.30 |
| | | Found | 76.29 | 5.16 |

REFERENCE EXAMPLE 11

(Reagent 1) (3-Dimethylaminopropyl)-triphenylphosphonium bromide hydrobromide

In this example, 350.0 g of triphenylphosphine and 270.0 g of dibromopropane are suspended in 700 ml of toluene and the suspension is heated at reflux for 25 hours. After allowing the suspension to stand for cooling, the formed product is separated by filtration and washed with 2 l of toluene to obtain 550.0 g of (3-bromopropyl)-triphenylphosphonium bromide hydrobromide having m.p. 233–234° C.

Then, 100.0 g of (3-bromopropyl)-triphenylphosphonium bromide hydrobromide is suspended in 500 ml of ethanol and 300 ml of 50% aqueous dimethylamine solution is added thereto. After heating the mixture at reflux for 10 minutes, the mixture is allowed to stand for cooling. The solvent is distilled away under reduced pressure and the resultant crude product is recrystallized from ethanol to obtain 64.0 g of the desired product having the physicochemical properties as identified in Table 8.

REFERENCE EXAMPLES 12–14

(Reagent 2) (3-Diethylaminopropyl)-triphenylphosphonium bromide hydrobromide.½ hydrate
(Reagent 3) (4-Dimethylaminobutyl)-triphenylphosphonium bromide hydrobromide
(Reagent 4) (3-Pyrrolidinopropyl)-triphenylphosphonium bromide hydrobromide.½ hydrate The above-captioned compounds are prepared according to the same manner as in Reference example 11 and the physicochemical properties are shown in Table 8.

TABLE 8

| Reagent | Melting point (°C.) | Elementary analysis (%) | | | |
|---|---|---|---|---|---|
| 1 | 287–289 (Ethanol) | as $C_{23}H_{28}NPBr_2$ | C | H | N |
| | | Calculated | 54.24 | 5.54 | 2.75 |
| | | Found | 54.12 | 5.63 | 2.93 |
| 2 | 228–230 (Isopropanol) | as $C_{25}H_{32}NPBr_2·½H_2O$ | C | H | N |
| | | Calculated | 55.33 | 6.05 | 2.58 |
| | | Found | 55.31 | 6.19 | 2.68 |
| 3 | 255–257 (Isopropanol) | as $C_{24}H_{30}NPBr_2$ | C | H | N |
| | | Calculated | 55.09 | 5.78 | 2.68 |
| | | Found | 55.04 | 5.91 | 2.62 |
| 4 | 291–293 (Ethanol) | as $C_{25}H_{30}NPBr_2·½H_2O$ | C | H | N |
| | | Calculated | 55.17 | 5.74 | 2.57 |
| | | Found | 55.18 | 5.95 | 2.66 |

EXAMPLE 1

Ethyl 11-(3-dimethylaminopropylidene)-6,11-dihydrodibenz[b,e]oxepin-2-carboxylate (Compound 2)

Process A:
N-(1,1-dimethyl-2-hydroxyethyl)-11-oxo-6,11-dihydrodibenz[b,e]oxepin-2-carboxamide In this process, 12.5 g of 6,11-dihydro-11-oxodibenz[b,e]oxepin-2-carboxylic acid is dissolved in 300 ml of methylene chloride and 8.9 g of thionyl chloride is dropwise added to the solution under ice-cooling. After stirring the mixture at room temperature for two hours, the solvent is distilled away under reduced pressure. To the obtained residue are added 100 ml of toluene and 32.4 g of 2-amino-2-methyl-propanol, and the mixture is stirred at 50° C. for 3 hours.

The mixture is extracted with 500 ml of ethyl acetate, and washed with saturated aqueous sodium bicarbonate solution and saturated aqueous sodium chloride solution in order. The mixture is dried over anhydrous sodium sulfate and the solvent is distilled away under reduced pressure. The crude product is recrystallized from toluene to obtain 8.3 g of the desired product as a white crystal.

Melting point: 155–159° C.

NMR (CDCl$_3$ +DMSO-d$_6$, δ, ppm): 1.38(s, 6H), 3.53(s, 2H), 5.25(s, 2H), 6.91–8.68(m, 7H)

Process B:
2-(4,4-Dimethyl-2-oxazoline-2-yl)-11-oxo-6,11-dihydrodibenz[b,e]oxepin In this process, 8.0 g of N-(1,1-dimethyl-2-hydroxyethyl)-11-oxo-6,11-dihydrodibenz[b,e]oxepin-2-carboxamide is suspended in 100 ml of methylene chloride. To the suspension is added 3.6 g of thionyl chloride under a nitrogen atmosphere and ice-cooling and the mixture is stirred at room temperature for one hour. To the mixture is added 300 ml of methylene chloride, and the mixture is washed with saturated aqueous sodium bicarbonate solution and dried over anhydrous magnesium sulfate. The solvent is distilled away under reduced pressure and the residue is purified by column chromatography on silica gel (eluent: hexane:ethyl acetate=2:1 ). The resultant crude product is recrystallized from hexane to obtain 6.3 g of the desired product as a white crystal.

Melting point: 122° C.

NMR (CDCl$_3$, δ, ppm): 1.37(s, 6H), 4.06(s, 2H), 5.14(s, 2H), 6.84–8.89(m, 7H)

Elementary analysis (%): as $C_{19}H_{17}O_3N$:
Calculated: C 74.25, H 5.58, N 4.56,
Found: C 74.23, H 5.55, N 4.59.

Process C:
11-(3-Dimethylaminopropyl)-11-hydroxy-2-(4,4-dimethyl-2-oxazoline-2-yl)-6,11-dihydrodibenz[b,e]oxepin To a solution of 3-dimethylaminopropyl magnesium chloride obtained by reacting 1.2 g of magnesium with 6.0 g of 3-dimethylaminopropyl chloride in 80 ml of tetrahydrofuran under a nitrogen atmosphere using dibromoethane as a catalyst is dropwise added under ice-cooling 80 ml of tetrahydrofuran solution of 7.6 g of 2-(4,4-dimethyl-2-oxazoline-2-yl)-11-oxo-6,11-dihydrodibenz[b,e]oxepin.

After stirring the mixture at room temperature overnight, aqueous ammonium chloride solution is added thereto and then the mixture is neutralized with aqueous 4N-hydrochloric acid solution. The solvent is distilled away under reduced pressure. To the residue is added aqueous 4N-hydrochloric acid solution to adjust the pH of the solution to 1. After washing the mixture with 200 ml of diethyl ether, aqueous 10N-sodium hydroxide solution is added to adjust the pH of the mixture to 13. The mixture is extracted with 200 ml of methylene chloride and the extract is washed with saturated aqueous sodium bicarbonate solution and saturated aqueous sodium chloride solution in order. After drying the solution over anhydrous sodium sulfate, the solvent is distilled away under reduced pressure. The residue is purified by column chromatography on silica gel (eluent: hexane:ethyl acetate triethylamine=10:10:1 ). The resultant crude product is triturated with isopropyl ether to obtain 6.1 g of the desired product as a white solid.

Melting point: 166–167° C.

NMR (CDCl$_3$, δ, ppm): 1.30(s, 8H), 2.18(s, 8H), 3.98 (s, 2H), 4.97 and 5.46(ABq, J=15.1 Hz, 2H), 6.65–8.49(m, 7H)

Process D: Ethyl 11-(3-dimethylaminopropylidene)-6,11-dihydrodibenz[b,e]oxepin-2-carboxylate In this process, 6.1 g of 11-(3-dimethylaminopropyl)-11-hydroxy-2-(4,4-dimethyl-2-oxazoline-2-yl)-6,11-dihydrodibenz[b,e]oxepin is dissolved in 300 ml of ethanol. To the solution are added 0.6 g of p-toluenesulfonic acid and 30 ml of water and the mixture is heated at reflux for 4 hours. The solvent is distilled away under reduced pressure to obtain a crude product of 11-(3-dimethylaminopropylidene)-6,11-dihydrodibenz[b,e]oxepin-2-carboxylic acid. The crude product is dissolved in 300 ml of ethanol and 20 ml of concentrated sulfuric acid is added thereto. The mixture is heated at reflux for 15 hours.

The solvent is distilled away under reduced pressure. To the resultant residue is added 200 ml of water and the mixture is washed with diethyl ether. The pH of the mixture is adjusted to 12.0 with aqueous 10N-sodium hydroxide solution and the mixture is extracted with 300 ml of methylene chloride. The extract is washed with saturated aqueous sodium bicarbonate solution and saturated aqueous sodium chloride solution in order. After drying the extract over anhydrous sodium sulfate, the solvent is distilled away under reduced pressure and the resultant residue is purified by column chromatography on silica gel (eluent: ethyl acetate:triethylamine=10:1 ) to obtain 1.4 g of the desired product as a colorless oily matter.

IR (neat, cm$^{-1}$): 2950, 2775, 1715, 1250, 1120, 1010
Mass spectrum (m/z): 351 (M$^+$)

EXAMPLE 2

11-(3-Dimethylaminopropylidene)-2-(2-triphenylmethyloxymethyl)-6,11-dihydrodibenz[b,e]oxepin (Compound 32)

Process A:
11-Hydroxy-2-(2-hydroxyethyl)-6,11-dihydrodibenz[b,e]oxepin

In this process, 20 g of methyl 11-oxo-6,11-dihydrodibenz[b,e]oxepin-2-acetate is dissolved in 500 ml of tetrahydrofuran. To the solution is added 6.0 g of lithium alminium hydroxide and the mixture is stirred at room temperature for one hour. After decomposing an excess of the reagent by the addition of water to the solution, the mixture is filtered to remove an inorganic salts and the filtrate is concentrated to dryness under reduced pressure to obtain 17.7 g of the desired product as a white solid.

Melting point: 132–136° C.

NMR (CDCl$_3$+DMSO-d$_6$+D$_2$O, δ, ppm): 2.59(t, 2H, J=6.8Hz), 3.55(t,2H, J=6.8Hz), 4.89 and 5.71(ABq, 2H, J=12.6Hz), 5.60(s, 1H), 6.46–7.49(m, 7H)

Process B:
11-Hydroxy-2-(2-triphenylmethyloxyethyl)-6,11-dihydrodibenz[b,e]oxepin In this process, 17.2 g of 11-hydroxy-2-(2-hydroxyethyl)-6,11-dihydrodibenz[b,e]oxepin is dissolved in 50 ml of pyridine. To the solution is added 30 g of triphenylchloromethane and the mixture is stirred at 50° C. for 5 hours. After adding water and stirring the mixture for 2 hours, the solvent is distilled away under reduced pressure. The mixture is extracted with 1000 ml of ethyl acetate, washed with saturated aqueous sodium chloride solution, and dried over anhydrous sodium sulfate. The solvent is distilled away under reduced pressure and the resultant residue is purified by column chromatography on silica gel (eluent: hexane:ethyl acetate=3:1 ) to obtain 21.7 g of the desired product as a colorless amorphous.

NMR (CDCl$_3$+D$_2$O, δ, ppm): 2.47–2.95(m, 2H), 2.96–3.45(m, 2H), 4.87 and 5.71(ABq, 2H, J=13.2Hz), 5.43(s, 1H), 6.33–7.51(m, 22H)

Process C:
11-Oxo-2-(2-triphenylmethyloxyethyl)-6,11-dihydrodibenz[b,e]oxepin

In this process, 10 g of 11-hydroxy-2-(2-triphenylmethyloxyethyl)-6,11-dihydrodibenz[b,e]oxepin is dissolved in a solution comprising 800 ml of acetone, 1000 ml of water, 20 ml of saturated aqueous magnesium sulfate solution and 0.2 g of disodium phosphate. To the solution is dropwise added 2.6 g of aqueous sodium permanganate solution and the mixture is stirred at room temperature for 4.5 hours. Then, 100 ml of methanol is added thereto and the mixture is heated at reflux for 3 hours. After allowing the mixture to stand for cooling, the mixture is filtered and the filtrate is extracted with 1000 ml of ethyl acetate, washed with saturated aqueous sodium chloride solution and dried over anhydrous sodium sulfate. The solvent is distilled away under reduced pressure and the resultant crude product is recrystallized from isopropanol to obtain 8.0 g of the desired product having melting point of 132–134° C. as a white crystal.
Elementary analysis (%): as C$_{35}$H$_{28}$O$_3$
Calculated: C 84.65, H 5.68,
Found: C 84.56, H 5.67.
NMR (CDCl$_3$, δ, ppm): 2.61–3.04(m, 2H), 3.05–3.46 (m, 2H), 5.01(s, 2H), 6.63–8.07(m, 22H)

Process D:
11-(3-Dimethylaminopropyl)-11-hydroxy-2-(2-triphenylmethyloxyethyl)-6,11-dihydrodibenz[b,e]oxepin To a solution of 3-dimethylaminopropyl magnesium chloride obtained by reacting 0.2 g of magnesium with 1.0 g of 3-dimethylaminopropyl chloride in 10 ml of tetrahydrofuran under a nitrogen atmosphere using dibromoethane as a catalyst, is dropwise added a solution obtained by dissolving 2.0 g of 11-oxo-2-(2-triphenylmethyloxyethyl)-6,11-dihydrodibenz[b,e]oxepin in 10 ml of tetrahydrofuran under ice cooling and the mixture is stirred at room temperature for one day. Aqueous ammonium chloride solution is added thereto and the pH of the mixture is adjusted to 7.0 with aqueous 4N-hydrochloric acid solution. The solvent is distilled away under reduced pressure. The mixture is extracted with 200 ml of methylene chloride and washed with saturated aqueous sodium bicarbonate solution and saturated aqueous sodium chloride solution in order. After drying the extract over anhydrous sodium sulfate, the solvent is distilled away under reduced pressure. The resultant residue is purified by column chromatography on silica gel (eluent: hexane:ethyl acetate:triethylamine=10:10:1 ) to obtain 1.2 g of the desired product as a colorless amorphous.
NMR (CDCl$_3$, δ, ppm): 0.85–1.83(m, 4H), 2.08(s, 6H), 2.67–3.44(m, 6H), 4.94 and 5.36(ABq, 2H, J=15.8Hz), 6.63–8.13(m, 22H)
Mass spectrum (m/z): 583 (M$^+$)

Process E:
11-(3-Dimethylaminopropylidene)-2-(2-triphenylmethyloxyethyl)-6,11-dihydrodibenz[b,e]oxepin In this process, 1.2 g of 11-(3-dimethylaminopropyl)-11-hydroxy-2-(2-triphenylmethyloxyethyl)-6,11-dihydrodibenz[b,e]oxepin is dissolved in 50 ml of pyridine. To the solution is dropwise added 0.8 g of phosphorusoxychloride under a nitrogen atmosphere and ice-cooling. After stirring the mixture at room temperature for one hour, the solvent is distilled away under reduced pressure. The residue is extracted with 100 ml of methylene chloride, and washed with saturated aqueous sodium bicarbonate solution and saturated aqueous sodium chloride solution in order. After drying the mixture over anhydrous sodium sulfate, the solvent is distilled away under reduced pressure. The resultant residue is purified by column chromatography on silica gel (eluent: hexane:ethylacetate:triethylamine=10:10:1 ) to obtain 0.82 g of the desired product as a colorless oily matter.
NMR (CDCl$_3$, δ, ppm): 2.16(s, 6H), 2.30–2.40(m, 4H), 2.79(t, 2H, J=6Hz), 3.24(t, 2H, J=6Hz), 5.97 (t, 1H, J=7Hz), 6.60–7.40(m, 22H), (trans form)
Mass spectrum (m/z): 565 (M$^+$)

EXAMPLE 3

11-(3-Dimethylaminopropylidene)-2-(2-hydroxyethyl)-6,11-dihydrodibenz[b,e]oxepin (Compound 31)

In this example, 0.92 g of 11-(3-dimethylaminopropylidene)-2-(2-triphenylmethyloxyethyl)-6,11-dihydrodibenz[b,e]oxepin is dissolved in a mixed solvent of 20 ml of water and 20 ml of dioxane. To the solution is added 60 mg of p-toluene sulfonic acid and the mixture is heated at reflux for two hours. The solvent is distilled away under reduced pressure and the residue is extracted with 200 ml of ethylacetate, washed with saturated aqueous sodium bicarbonate solution and saturated aqueous sodium hydrochloride solution in oder and dried over anhydrous sodium sulfate. The solvent is distilled away under reduced pressure. The resultant residue is purified by column chromatography on silica gel (eluent: ethylacetate triethylamine=10:1 ) to obtain 0.4 g of the desired product.
Cis form white solid,
Melting point: 100–102° C. (diethylether)
NMR (CDCl$_3$, δ, ppm): 2.32(s, 6H), 2.30–2.70(m, 4H), 2.76(t, 2H, J=6Hz), 3.78(t, 2H, J=6Hz), 5.66(t, 1H, J=7Hz), 6.80–7.40(m, 7H)
Mass spectrum: 323 (M$^+$)
Trans form white solid,
Melting point: 96°–97° C. (diethylether)
NMR (CDCl$_3$, δ, ppm): 2.21(s, 6H), 2.30–2.70(m, 4H), 2.76(t, 2H, J=6Hz), 3.78(t, 2H, J=6Hz), 6.01(t, 1H, J=7Hz), 6.68–7.40(m, 7H)
Mass spectrum (m/z): 323 (M$^+$)

EXAMPLE 4

11-(3-Dimethylaminopropylidene)-6,11-dihydrodibenz [b,e]oxepin-2-acetic acid (Compound 20)

In this Example, 2.2 g of 11-(3-dimethylaminopropylidene)-2-(2-hydroxyethyl)-6,11-dihydrodibenz[b,e]oxepin is dissolved in 100 ml of acetone. The Jones reagent is added to the solution until the reaction solution shows an orange color and the mixture is stirred at room temperature for one hour. Sodium bicarbonate is added thereto and an inorganic substance is removed by filtration. The solvent of the filtrate is distilled away under reduced pressure to obtain the desired product. The physicochemical properties of the product coincide with those of the product obtained in Example 35.

EXAMPLE 5

Methyl 11-(3-dimethylaminopropylidene)-6,11-dihydrodibenz[b,e]oxepin-2-carboxylate (Compound 1)

In this Example, 45 g of (3-dimethylaminopropyl)triphenylphosphonium bromide hydrobromide is suspended in 200 ml of tetrahydrofuran under a nitrogen atmosphere and 82 ml of 1.6N-n-butyl lithium hexane solution is added thereto under ice-cooling. The mixture is stirred under ice-cooling for one hour. To the mixture is dropwise added under ice-cooling a solution obtained by dissolving 10 g of methyl 11-oxo-6,11-dihydrodibenz[b,e]oxepin-2-carboxylate in 200 ml of tetrahydrofuran. After stirring the mixture at room temperature for 2 hours, the mixture is extracted with 800 ml of ethyl acetate. After washing the extract with saturated aqueous sodium chloride solution and drying the extract over anhydrous sodium sulfate, the solvent is distilled away under reduced pressure. The residue is purified by column chromatography on silica gel (eluent: hexane:ethyl acetate:triethylamine=10:10:1) to obtain 2.0 g of trans form and 5.6 g of cis form of the desired product.

Cis form: NMR (CDCl$_3$, δ, ppm): 2.23(s, 6H), 2.17–2.81(m, 4H), 5.28(bs, 2H), 5.61(t, 1H), 6.80–8.10(m, 7H)

Trans form: NMR (CDCl$_3$, δ, ppm): 2.15(s, 6H), 2.17–2.81(m, 4H), 5.00–5.50(broad, 2H), 6.06 (t, 1H), 6.70–8.10(m, 7H)

EXAMPLE 6

Methyl 11-(3-diethylaminopropylidene)-6,11-dihydrodibenz[b,e]oxepin-2-carboxylate (Compound 4)

The desired product is obtained by substituting (3-diethylaminopropyl)-triphenylphosphonium bromide hydrobromide.½ hydrate for (3-dimethylaminopropyl)-triphenylphosphonium bromide hydrobromide in Example 5.

EXAMPLE 7

Methyl 11-(3-pyrrolidinopropylidene)-6,11-dihydrodibenz[b,e]oxepin-2-carboxylate (Compound 6)

The desired product is obtained by substituting (3-pyrrolidinopropyl)-triphenylphosphonium bromide hydrobromide.½ hydrate for (3-dimethylaminopropyl)-triphenylphosphonium bromide hydrobromide in Example 5.

EXAMPLE 8

Methyl 11-(4-dimethylaminobutylidene)-6,11-dihydrodibenz[b,e]oxepin-2-carboxylate (Compound 8)

The desired product is obtained by substituting (4-dimethylaminopropyl)-triphenylphosphonium bromide hydrobromide for (3-dimethylaminopropyl)-triphenylphosphonium bromide hydrobromide in Example 5.

EXAMPLE 9

Methyl 11-(3-dimethylaminopropylidene)-6,11-dihydrodibenz[b,e]oxepin-2-acetate (Compound 18)

In this example, 48 g of (3-dimethylaminopropyl)-triphenylphosphonium bromide hydrobromide is suspended in 200 ml of tetrahydrofuran under a nitrogen atmosphere and 80 ml of 1.6N-n-butyl lithium hexane solution is added thereto under ice-cooling. The mixture is stirred under ice-cooling for one hour. A solution obtained by dissolving 5.0 g of 11-oxo-6,11-dihydrodibenz [b,e]oxepin-2-acetic acid in 120 ml of tetrahydrofuran is dropwise added under ice-cooling. After stirring the mixture at room temperature for two hours, the solvent is distilled away under reduced pressure. Then, 200 ml of water is added to the residue and the mixture is washed with 200 ml of diethyl ether. The pH of the mixture is adjusted to 1 with aqueous 4N-hydrochloric acid solution and the mixture is washed with diethyl ether.

Then, aqueous 10N-sodium hydrooxide solution is added thereto to adjust the pH of the mixture to 7 and the solvent is distilled away under reduced pressure. The resultant residue is dissolved in 400 ml of methanol and 5 g of p-toluene sulfonic acid is added thereto. After heating the mixture at reflux for two hours, the solvent is distilled away under reduced pressure. The residue is extracted with 300 ml of ethyl acetate, washed with saturated aqueous sodium bicarbonate solution and saturated aqueous sodium chloride solution in order and dried over anhydrous sodium sulfate.

The solvent is distilled away under reduced pressure and the resultant residue is purified by column chromatography on silica gel (eluent: hexane:ethyl acetate:triethylamine=10:10:1) to obtain 4.0 g of the desired product as a colorless oily matter.

Cis form
NMR (CDCl$_c$, δ, ppm): 2.06–2.67(m, 4H), 2.16(s, 6H), 3.46(s, 2H), 3.58(s, 3H), 5.08(bs, 2H), 5.69 (t, 1H, J=7Hz), 6.53–7.30(m, 7H)

Trans form
NMR (CDCl$_3$, δ, ppm): 2.06–2.67(m, 4H), 2.16(s, 6H), 3.46(s, 2H), 3.58(s, 3H), 5.08(bs, 2H), 6.06 (t, 1H, J=7Hz), 6.53–7.30(m, 7H)

EXAMPLE 10

Methyl 11-(4-dimethylaminobutylidene)-6,11-dihydrodibenz[b,e]oxepin-2-acetate (Compound 21)

The desired product is obtained by substituting (4-dimethylaminobutyl)-triphenylphosphonium bromide hydrobromide for (3-dimethylaminopropyl)-triphenylphosphonium bromide hydrobromide in Example 9.

EXAMPLE 11

Methyl 11-(3-pyrrolidinopropylidene)-6,11-dihydrodibenz[b,e]oxepin-2-acetate (Compound 23)

The desired product is obtained by substituting (3-pyrrolidinopropyl)-triphenylphosphonium bromide hydrobromide. ½ hydrate for (3-dimethylaminopropyl)-triphenylphosphonium bromide hydrobromide in Example 9.

EXAMPLE 12

Methyl 3-[11-(3-dimethylaminopropylidene)-6,11-dihydrodibenz[b,e]oxepin-2-yl]-propionate (Compound 27)

The desired product is obtained by substituting 3-(11-oxo-6,11-dihydrodibenz[b,e]oxepin-2-yl)-propionic acid for 11-oxo-6,11-dihydrodibenz[b,e]oxepin-2-acetic acid in Example 9.

EXAMPLE 13

Methyl 11-(3-dimethylaminopropylidene)-6,11-dihydrodibenz[b,e]oxepin-3-acetate (Compound 29)

The desired product is obtained by substituting 11-oxo-6,11-dihydrodibenz[b,e]oxepin-3-acetic acid for 11-oxo-6,11-dihydrodibenz[b,e]oxepin-2-acetic acid in Example 9.

EXAMPLE 14

Methyl 11-(2-dimethylaminoethyl)imino-6,11-dihydrodibenz[b,e]oxepin-2-acetate (Compound 36)

In this example, 22.0 g of methyl 11-oxo-6,11-dihydrodibenz[b,e]oxepin-2-acetate and 68.7 g of N,N-dimethylethylenediamine are dissolved in 700 ml of dried benzene. To the solution is dropwise added a solution of 17.2 ml of titanium tetrachloride in 40 ml of dried benzene and the mixture is stirred at room temperature overnight. A saturated aqueous sodium bicarbonate solution is added thereto. After removing an insoluble solid by filtration, the filtrate is extracted with 500 ml of ethylacetate, washed with saturated aqueous sodium bicarbonate solution and saturated aqueous sodium chloride solution in order, and dried over anhydrous sodium sulfate. The solvent is distilled away under reduced pressure and the residue is purified by column chromatography on silica gel with ethylacetate/triethylamine (10/1) as an eluent to obtain 13.8 g of the desired product as a colorless oily matter.

NMR (CDCl$_3$, δ, ppm): 2.14(s, 6H), 2.63(t, 2H, J=6.9Hz),
3.51(s, 2H), 3.58(s, 3H), 3.38-3.80 (m, 2H), 5.04(bs, 2H), 6.56-7.60(m, 7H)

IR (neat, cm$^{-1}$) 2950, 1740, 1630, 1305, 1015
Mass spectrum (m/z): 352 (M$^+$)

EXAMPLE 15

Methyl-11-(2-diethylaminoethyl)imino-6,11-dihydrodibenz[b,e]oxepin-2-carboxylate (Compound 34)

The desired product is obtained by substituting methyl 11-oxo-6,11-dihydrodibenz[b,e]oxepin-2-carboxylate for methyl 11-oxo-6,11-dihydrodibenz[b,e]oxepin-2-acetate in Example 14 as a colorless oily matter.

Mass spectrum (m/z): 366 (M$^+$) for $C_{22}H_{26}O_3N_2$

EXAMPLE 16

Ethyl 11-(2-diethylaminoethyl)imino-6,11-dihydrodibenz[b,e]oxepin-2-acetate (Compound 38)

The desired product is obtained by substituting N,N-diethylethylenediamine for N,N-dimethylethylenediamine in Example 14 as a colorless oily matter.

Mass spectrum (m/z): 380 (M$^+$) for $C_{23}H_{28}O_3N_2$

EXAMPLE 17

Methyl 11-(3-dimethylaminopropyl)imino-6,11-dihydrodibenz[b,e]oxepin-2-acetate (Compound 40)

The desired product is obtained by substituting N,N-dimethylpropylenediamine for N,N-dimethylethylenediamine in Example 14 as a colorless oily matter.

Mass spectrum (m/z): 366 (M$^+$) for $C_{22}H_{26}O_3N_2$

EXAMPLE 18

Methyl 3-[11-(2-dimethylaminoethyl)imino-6,11-dihydrodibenz[b,e]oxepin-2-yl]-propionate (Compound 42)

The desired product is obtained by substituting 3-(11-oxo-6,11-dihydrodibenz[b,e]oxepin-2-yl)-propionic acid for methyl 11-oxo-6,11-dihydrodibenz[b,e]oxepin-2-acetate in Example 16 as a colorless oily matter.

Mass spectrum (m/z): 394 (M$^+$) for $C_{24}H_{30}O_3N_2$

EXAMPLE 19

Methyl 2-[11-(2-dimethylaminoethyl)imino-6,11-dihydrodibenz[b,e]oxepin-2-yl]-propionate (Compound 44)

The desired product is obtained by substituting 2-(11-oxo-6,11-dihydrodibenz[b,e]oxepin-2-yl)-propionic acid for methyl 11-oxo-6,11-dihydrodibenz[b,e]oxepin-2-acetate in Example 14 as a colorless oily matter.

Mass spectrum (m/z): 366 (M$^+$) for $C_{22}H_{26}O_3N_2$

EXAMPLE 20

Methyl 11-(2-dimethylaminoethyl)imino-6,11-dihydrodibenz[b,e]oxepin-3-acetate (Compound 46)

The desired product is obtained by substituting 11-oxo-6,11-dihydrodibenz[b,e]oxepin-3-acetic acid for methyl 11-oxo-6,11-dihydrodibenz[b,e]oxepin-2-acetate in Example 14 as a colorless oily matter.

Mass spectrum (m/z): 352 (M$^+$) for $C_{21}H_{24}O_3N_2$

EXAMPLE 21

Methyl 11-(3-dimethylaminopropyl)imino-6,11-dihydrodibenz[b,e]oxepin-3-acetate (Compound 48)

The desired product is obtained by substituting 11-oxo-6,11-dihydrodibenz[b,e]oxepin-3-acetic acid for 11-oxo-6,11-dihydrodibenz[b,e]oxepin-2-acetic acid in Example 17 as a colorless oily matter.

Mass spectrum (m/z): 366 (M$^+$) for $C_{22}H_{26}O_3N_2$

EXAMPLE 22

Methyl 11-[2-(4-methylpiperazino)ethylidene]-6,11-dihydrodibenz[b,e]oxepin-2-carboxylate (Compound 10)

In this example, 1.5 ml of 4-methylpiperazine and 0.37 g of p-formaldehyde are dissolved in 100 ml of tetrachloroethane. To the solution is dropwise added 5 ml of trifluoroacetic acid. After stirring the mixture at 60° C. for 2 hours, a solution obtained by dissolving 1.8 g of methyl 11-methylene-6,11-dihydrodibenz[b,e]oxepin-2-carboxylate in 30 ml of tetrachloroethane is dropwise added thereto and the mixture is stirred at 90° C. for 3 hours.

The mixture is concentrated to dryness under reduced pressure and aqueous 4N-hydrochloric acid solution is added to the residue to adjust the pH to 1. After washing the solution with diethylether, aqueous 10N-sodium hydroxide solution is added thereto to adjust the pH to 13. The mixture is extracted with 200 ml of methylene chloride, washed with saturated aqueous sodium chloride solution and dried over anhydrous sodium sulfate. The solvent is distilled away under reduced pressure. The residue is purified by column chromatography on silica gel (eluent: hexane:ethyl acetate:triethylamine=5:5:1) to obtain 2.2 g of the desired product as a colorless oily matter.

Cis form: NMR (CDCl$_3$, δ, ppm): 2.24(s, 3H), 2.45(s, 8H), 2.94–3.32(m, 2H), 3.84(s, 3H), 5.22(bs, 2H), 5.85(t, 1H, J=6.8Hz), 6.66–8.07(m, 7H)

Mass spectrum (m/z): 378 (M$^+$)

Trans form: NMR (CDCl$_3$, δ, ppm): 2.24(s, 3H), 2.45(s, 8H), 2.94–3.32(m, 2H), 3.84(s, 3H), 5.22(bs, 2H), 6.22(t, 1H, J=6.8Hz)

Mass spectrum (m/z): 378 (M$^+$)

EXAMPLE 23

Methyl 11-(2-morpholinoethylidene)-6,11-dihydrodibenz[b,e]oxepin-2-carboxylate (Compound 12)

The desired product is obtained by substituting morpholine for 4-methylpiperazine in Example 22.

EXAMPLE 24

Methyl 11-(2-thiomorpholinoethylidene)-6,11-dihydrodibenz[b,e]oxepin-2-carboxylate (Compound 14)

The desired product is obtained by substituting thiomorpholine for 4-methylpiperazine in Example 22.

EXAMPLE 25

Methyl 11-(2-pyrrolidinoethylidene)-6,11-dihydrodibenz[b,e]oxepin-2-carboxylate (Compound 16)

The desired product is obtained by substituting pyrrolidine for 4-methylpiperazine in Example 22.

EXAMPLE 26

Methyl 11-(2-piperidinoethylidene)-6,11-dihydrodibenz[b,e]oxepin-2-carboxylate (Compound 17)

The desired product is obtained by substituting piperidine for 4-methylpiperazine in Example 22.

EXAMPLE 27

Methyl 11-[2-(4-methylpiperazino)ethylidene]-6,11-dihydrodibenz[b,e]oxepin-2-acetate (Compound 25)

The desired product is obtained by substituting methyl 11-methylene-6,11-dihydrodibenz[b,e]oxepin-2-acetate for methyl 11-methylene-6,11-dihydrodibenz[b,e]oxepin-2-carboxylate in Example 22.

EXAMPLE 28

11-(3-Dimethylaminopropylidene)-6,11-dihydrodibenz[b,e]oxepin-2-carboxylic acid (Compound 3)

In this example, 26.1 g of methyl 11-(3-dimethylaminopropylidene)-6,11-dihydrodibenz[b,e]oxepin-2-carboxylate is dissolved in a mixed solvent of 500 ml of methanol and 30 ml of water and 6.2 g of sodium hydroxide is added thereto. The mixture is heated at reflux for two hours. After allowing the mixture to stand for cooling, aqueous 4N-hydrochloric acid solution is added thereto to adjust the pH to 7 and the mixture is concentrated under reduced pressure. The concentrate is purified by column chromatography on high porous polymer (HP-20) (eluent: water:methanol=1:2) to obtain 25.0 g of the desired product.

Cis form white crystal
Melting point: 162–164° C.
NMR (DMSO-d$_6$, δ, ppm): 2.28(s, 6H), 2.40–2.70(m, 4H),
5.20–5.40(broad, 2H), 5.72(t, 1H, J=7.0Hz),
6.85–7.90(m, 7H)
IR (KBr disk, cm$^{-1}$) 3400, 1610, 1370, 1220, 1005
Elemental analysis (%): as C$_{20}$H$_{21}$O$_3$N.$\frac{1}{2}$ H$_2$O

|  | C | H | N |
|---|---|---|---|
| Found: | 73.00 | 6.67 | 4.14 |
| Calculated: | 72.93 | 6.63 | 4.25 |

Trans form white crystal
Melting point: 242°–244° C.
NMR (DMSO-d$_6$, δ, ppm) 2.25(s, 6H), 2.40–2.70(m, 4H),
5.20–5.40(broad, 2H), 6.09(t, 1H, J=7.0Hz),
6.78–7.90(m, 7H)
IR (KBr disk, cm$^{-1}$) 3400, 1610, 1380, 1222, 1010
Elemental analysis (%):

|  | C | H | N |
|---|---|---|---|
| Found: | 74.30 | 6.60 | 4.30 |
| Calculated: | 74.28 | 6.55 | 4.30 |

EXAMPLES 29–34

11-(3-Diethylaminopropylidene)-6,11-dihydrodibenz[b,e]oxepin-2-carboxylic acid (Compound 5)
11-(3-Pyrrolidinopropylidene)-6,11-dihydrodibenz[b,e]oxepin-2-carboxylic acid (Compound 7)
11-(4-Dimethylaminobutylidene)-6,11-dihydrodibenz[b,e]oxepin-2-carboxylic acid (Compound 9)
11-[2-(4-Methylpiperazino)ethylidene]-6,11-dihydrodibenz[b,e]oxepin-2-carboxylic acid (Compound 11)
11-(2-Morpholinoethylidene)-6,11-dihydrodibenz[b,e]oxepin-2-carboxylic acid (Compound 13)

11-(2-Thiomorpholinoethylidene)-6,11-dihydrodibenz[b,e]oxepin-2-carboxylic acid (Compound 15)

These products are obtained by hydrolysis in the same manner as in Example 28.

| Compound | Melting point (°C.) | Elementary analysis (%) or Mass spectrum | | | |
|---|---|---|---|---|---|
| 5 | White solid 120–123 (Acetonitrile) | Cis: Trans = 7:3 As $C_{22}H_{25}O_3N$ | | | |
| | | | C | H | N |
| | | Found | 75.10 | 7.11 | 3.87 |
| | | Calculated | 75.19 | 7.17 | 3.99 |
| 7 | Colorless amorphous About 150 (Decomposition) | For $C_{22}H_{23}O_3N$ 349 ($M^+$) | | | |
| 9 | White solid 128–129 (Water) | Cis: Trans = 9:1, dihydrate As $C_{21}H_{23}NO_3 \cdot 2H_2O$ | | | |
| | | | C | H | N |
| | | Found | 67.61 | 7.03 | 4.00 |
| | | Calculated | 67.54 | 7.29 | 3.75 |
| 11 | White solid 150–153 (Water) | Cis: Trans = 1:9, dihydrate As $C_{22}H_{24}NO_3 \cdot 2H_2O$ | | | |
| | | | C | H | N |
| | | Found | 65.98 | 6.99 | 6.95 |
| | | Calculated | 65.98 | 7.05 | 7.00 |
| 13 | White solid 130–133 (Toluene) | Cis: Trans = 1:9 As $C_{21}H_{21}O_4N$ | | | |
| | | | C | H | N |
| | | Found | 71.52 | 6.11 | 3.81 |
| | | Calculated | 71.78 | 6.02 | 3.99 |
| 15 | Colorless amorphous About 140 | As $C_{21}H_{21}O_3NS$ 367 ($M^-$) | | | |

EXAMPLE 35

11-(3-Dimethylaminopropylidene)-6,11-dihydrodibenz[b,e]oxepin-2-acetic acid (Compound 20)

The product is obtained by hydrolysis as in the same manner as in Example 28.

Cis form white crystal
Melting point: 118°–120° C. (Isopropanol)
NMR (DMSO-$d_6$, δ, ppm): 2.16(s, 6H), 2.30–2.60(m, 4H),
4.04(s, 2H), 5.115(bs, 2H), 5.69(t, 1H, J=7Hz), 6.73–7.40(m, 7H)
Ir (KBr disk, cm$^{-1}$): 3400, 1580, 1225, 1005
Mass spectrum (m/z): 337 ($M^+$)
Elementary analysis (%): as $C_{21}H_{23}O_3N \cdot$monohydrate

| | C | H | N |
|---|---|---|---|
| Found | 70.77 | 7.36 | 3.74 |
| Calculated | 70.96 | 7.09 | 3.94 |

Trans form white crystal
Melting point: 158°–160° C. (Acetonitrile)
NMR (DMSO-$d_6$, δ, ppm): 2.05(s, 6H), 2.30–2.60(m, 4H), 4.04(s, 2H), 5.15(bs, 2H), 6.06(t, 1H, J=7Hz), 6.73–7.40(m, 7H)
IR (neat, cm$^{-1}$): 3380, 1575, 1220, 1005
Mass spectrum (m/z): 337 ($M^+$)
Elementary analysis (%): as $C_{21}H_{23}O_3N \cdot$monohydrate

| | C | H | N |
|---|---|---|---|
| Found | 71.06 | 6.66 | 3.92 |
| Calculated | 70.96 | 7.09 | 3.94 |

EXAMPLES 36–39

11-(4-Dimethylaminobutylidene)-6,11-dihydrodibenz[b,e]oxepin-2-acetic acid (Compound 22)
11-(3-Pyrrolidinopropylidene)-6,11-dihydrodibenz[b,e]oxepin-2-acetic acid (Compound 24)
11-[2-(4-Methylpiperazino)ethylidene]-6,11-dihydrodibenz[b,e]oxepin-2-acetic acid (Compound 26)
3-[11-(3-Dimethylaminopropylidene)-6,11-dihydrodibenz[b,e]oxepin-2-yl]-propionic acid (Compound 28)

These products are obtained by hydrolysis in the same manner as in Example 35. The physicochemical properties are shown in Table 9.

TABLE 9

| Compound | Melting point (°C.) | Elementary analysis (%) | | | |
|---|---|---|---|---|---|
| 22 | White solid 206–209 (Isopropanol) | Cis: Trans = 92:8 as $C_{22}H_{25}O_3N$ | | | |
| | | | C | H | N |
| | | Found | 75.20 | 7.28 | 4.02 |
| | | Calculated | 75.19 | 7.17 | 3.99 |
| 26 | White solid 206–209 (Isopropanol) | Cis: Trans = 1:9 as $C_{22}H_{25}O_3N$ | | | |
| | | | C | H | N |
| | | Found | 75.19 | 7.17 | 3.99 |
| | | Calculated | 75.15 | 7.28 | 3.96 |

Compound 28

Cis form white crystal
Melting point: 136°–138° C. (Isopropylether)
NMR (DMSO-$d_6$, δ, ppm): 2.32(m, 2H), 2.38(s, 6H), 2.44–2.56(m, 2H), 2.73(m, 4H), 5.15(bs, 2H), 5.50(m, 1H), 6.7–7.4(m, 7H)
IR (KBr disk, cm$^{-1}$): 3380, 1645
Mass spectrum (m/z): 351 ($M^+$)
Elementary analysis (%): as $C_{22}H_{25}NO_3$

| | C | H | N |
|---|---|---|---|
| Found | 74.83 | 7.31 | 3.97 |
| Calculated | 75.19 | 7.17 | 3.99 |

Trans form white crystal
Melting point: 148°–149° C. (Acetonitrile)
NMR (DMSO-$d_6$, δ, ppm): 2.05(s, 6H), 2.24(m, 2H), 2.35(m, 2H), 2.47(t, 2H, J=7.5Hz), 2.72(t, 2H, J=7.5Hz), 4.80–5.50(broad, 2H), 5.99(t, 1H, J=7.1Hz), 6.6–7.5(m, 7H)
IR (KBr disk, cm$^{-1}$): 3380, 1700
Mass spectrum: 351 ($M^+$)
Elementary analysis (%): as $C_{22}H_{25}NO_3 \cdot 1/5$ hydrate

| | C | H | N |
|---|---|---|---|
| Found | 74.53 | 7.20 | 4.32 |
| Calculated | 74.42 | 7.21 | 3.95 |

EXAMPLE 40

11-(2-Dimethylaminoethyl)imino-6,11-dihydrodibenz[- b,e]oxepin-2-acetic acid (Compound 37)

The desired product is obtained as a 8:92 mixture of cin-form and anti-form by hydrolysis in the same manner as in Example 27.

White crystal

Melting point: 174°–176° C. (as ½ hydrate)

NMR (DMSO-$d_6$, δ, ppm): 2.07(s, 6H), 2.30–2.80(m, 4H),
3.47(s, 2H), 4.90–5.30(broad, 2H), 6.74–7.62 (m, 7H)

IR (KBr disk, cm$^{-1}$): 3350, 1575, 1370, 1010

Elementary analysis (%): as $C_{20}H_{22}N_2O_3 \cdot \frac{1}{2}$ hydrate

|  | C | H | N |
|---|---|---|---|
| Found | 69.47 | 6.77 | 8.06 |
| Calculated | 69.14 | 6.67 | 8.06 |

EXAMPLES 41–47

11-(2-Diethylaminoethyl)imino-6,11-dihydrodibenz[- b,e]oxepin-2-carboxylic acid (Compound 35)

11-(2-Diethylaminoethyl)imino-6,11-dihydrodibenz[- b,e]oxepin-2-acetic acid (Compound 39)

11-(3-Dimethylaminopropyl)imino-6,11-dihydrodibenz[b,e]oxepin-2-acetic acid (Compound 41)

3-[11-(2-Diethylaminoethyl)imino-6,11-dihydrodibenz[- b,e]oxepin-2-yl]-propionic acid (Compound 43)

2-[11-(2-Dimethylaminoethyl)imino-6,11-dihydrodibenz[b,e]oxepin-2-yl]-propionic acid (Compound 45)

11-(2-Dimethylaminoethyl)imino-6,11-dihydrodibenz[- b,e]oxepin-3-acetic acid (Compound 47)

11-(3-Dimethylaminopropyl)imino-6,11-dihydrodibenz[b,e]oxepin-3-acetic acid (Compound 49)

The desired compounds are obtained by hydrolysis in the same manner as in Example 40. The physicochemical properties are shown in Table 10.

TABLE 10

| Compound | Melting point (°C.) | Elementary analysis (%) or Mass spectrum | | |
|---|---|---|---|---|
| 35 | White solid 198–200 (Isopropyl ether) | Cin: Anti = 1:1 as $C_{21}H_{24}O_3N_2$ | | |
|  |  | | C | H | N |
|  |  | Found | 71.66 | 6.90 | 7.82 |
|  |  | Calculated | 71.57 | 6.86 | 7.95 |
| 39 | White solid 161–162 (Ethyl acetate) | Anti: 98% as $C_{22}H_{26}O_3N_2$ | | |
|  |  | | C | H | N |
|  |  | Found | 72.25 | 7.24 | 7.58 |
|  |  | Calculated | 72.11 | 7.15 | 7.64 |
| 41 | White solid 171–173 (Isopropanol) | Anti: 97% as $C_{21}H_{24}O_3N_2$ | | |
|  |  | | C | H | N |
|  |  | Found | 71.35 | 6.92 | 7.69 |
|  |  | Calculated | 71.57 | 6.86 | 7.95 |
| 43 | Colorless Oily | as $C_{23}H_{28}O_3N_2$ 380 (M+) | | |
| 45 | White solid 132–135 (Water) | Anti > 95% as $C_{21}H_{24}O_3N_2$ | | |
|  |  | | C | H | N |
|  |  | Found | 71.39 | 6.99 | 7.91 |
|  |  | Calculated | 71.57 | 6.86 | 7.95 |
| 47 | White solid 194–195 (Decomposition) (Methanol) | Anti > 95% as $C_{20}H_{22}O_3N_2$ | | |
|  |  | | C | H | N |
|  |  | Found | 70.87 | 6.80 | 7.93 |
|  |  | Calculated | 70.98 | 6.55 | 8.28 |

TABLE 10-continued

| Compound | Melting point (°C.) | Elementary analysis (%) or Mass spectrum | | |
|---|---|---|---|---|
| 49 | White solid 174–175 (Decomposition) (Isopropanol) | Anti > 95% as $C_{21}H_{24}O_3N_2$ | | |
|  |  | | C | H | N |
|  |  | Found | 71.42 | 7.03 | 8.06 |
|  |  | Calculated | 71.57 | 6.86 | 7.95 |

EXAMPLE 48

Methyl 11-(3-dimethylaminopropyl)-6,11-dihydrodibenz[- b,e]oxepin-2-carboxylate (Compound 50) Process A:
11-Hydroxy-2-(4,4-dimethyl-2-oxazoline-2-yl)-6,11-dihydrodibenz[b,e]oxepin In this process, 2.40 g of 11-oxo-2-(4,4-dimethyl-2-oxazoline-2-yl)-6,11-dihydrodibenz[b,e]oxepin is dissolved in 100 ml of methanol and 0.3 g of sodium borohydride is added thereto. After stirring the mixture at room temperature for 30 minutes, the solvent is distilled away under reduced pressure. The residue is extracted with 200 ml of methylene chloride, washed with saturated aqueous sodium bicarbonate solution and saturated aqueous sodium chloride solution in order, and dried over anhydrous sodium sulfate and the solvent is distilled away under reduced pressure. The residue is recrystallized from toluene to obtain 2.06 g of the desired product as a white solid.

Melting point: 201°–203° C.

Process B:
11-(3-Dimethylaminopropyl)-2-[4,4-dimethyl-2-oxazoline-2-yl)-6,11-dihydrodibenz[b,e]oxepin In this process, 1.90 g of 11-hydroxy-2-(4,4-dimethyl-2-oxazoline-2-yl)-6,11-dihydrodibenz[b,e]oxepin is dissolved in 30 ml of methylene chloride and 0.7 ml of thionyl chloride is added thereto under ice-cooling. After stirring the mixture at room temperature for one hour, the solvent is distilled away under reduced pressure to obtain a crude product of 11-chloro-2-(4,4-dimethyl-2-oxazoline-2-yl)-6,11-dihydrodibenz[b,e]oxepin. The crude product as such is dissolved in 10 ml of tetrahydrofuran without purification.

To the solution is dropwise added under a nitrogen atmosphere 3-dimethylaminopropyl magnesium chloride obtained in the same manner as in Process C of Example 1 until the raw material is used up. The reaction mixture is extracted with 100 ml of methylene chloride, washed with saturated aqueous sodium bicarbonate solution and saturated aqueous sodium chloride solution in order and dried over anhydrous sodium sulfate, and the solvent is distilled away under reduced pressure. The residue is purified by column chromatography on silica gel (eluent: hexane:ethyl acetate:triethylamine=10:10:1) to obtain 0.06 g of the desired product as a colorless oily matter.

Mass spectrum (m/z): 378 (M+) for $C_{24}H_{30}O_2N$

Process C: Methyl 11-(3-dimethylaminopropyl)-6,11-dihydrodibenz[- b,e]oxepin-2-carboxylate In this process, 60 mg of 11-(3-dimethylaminopropyl)-2-(4,4-dimethyl-2-oxazoline-2-yl)-6,11-dihydrodibenz[b,e]oxepin is dissolved in a mixed solvent of 20 ml of water and 20 ml of dioxane and 10 mg of p-toluenesulfonic acid is added thereto. After heating the mixture at reflux for 3 hours, the mixture is concentrated under reduced pressure. The concentrate is extracted with 100 ml of ethyl acetate, washed with saturated aqueous sodium bicarbonate solution and saturated aqueous sodium chloride solution in order and dried over anhydrous sodium sulfate, and the solvent is distilled away under reduced pressure. The residue is dissolved in a mixed solution of 30 ml of methanol and 10 ml of aqueous 1N-sodium hydroxide solution and the mixture is heated at reflux for 2 hours. After allowing the mixture to stand for cooling, the pH of the mixture is adjusted to 5.4 with aqueous 4N-hydrochloric acid solution.

The solvent is distilled away under reduced pressure and the residue is redissolved in 50 ml of methanol. After adding 10 mg of p-toluenesulfonic acid thereto, the mixture is heated at reflux for 3 hours and concentrated under reduced pressure. The residue is extracted with 100 ml of ethyl acetate, washed with saturated aqueous sodium bicarbonate solution and saturated aqueous sodium chloride solution in order and dried over anhydrous sodium sulfate and the solvent is distilled away under reduced pressure. The residue is developed on 3 sheets of preparative TLC (20 cm ×20 cm ×0.25 mm) with a mixed solvent (eluent: hexane:ethyl acetate:triethylamine=10:10:2). The band at $R_f=0.47$ is collected, and extracted with methylene chloride and the solvent is distilled away under reduced pressure to obtain 5.3 mg of the desired product as a colorless oily matter.

NMR (CDCl$_3$, δ, ppm): 1.20-1.40(m, 1H), 1.60-1.80 (m, 2H), 2.18(m, 2H), 2.56(s, 6H), 2.74(dd, 2H, J=6.6Hz and 9.5Hz), 3.90(s, 3H), 5.00 and 5.59 (ABq, 2H, J=14.2Hz), 6.96-7.88(m, 7H)

Mass spectrum (m/z): 325 (M$^+$) for $C_{20}H_{23}O_3N$
IR (neat, ν, cm$^{-1}$): 3400, 1710, 1610, 1110

EXAMPLE 49

½ Fumarate .1/5 hydrate of Compound 3 (Compound 3')

In this example, 3.95 g of 11-(3-dimethylaminopropylidene)-6,11-dihydrodibenz[b,e]oxepin-2-carboxylic acid (Compound 3) is dissolved in 100 ml of acetone and 1.42 g of fumaric acid is added thereto. The mixture is stirred at room temperature. The deposited crystals are recovered by filtration and recrystallized from isopropanol to obtain 4.15 g of the desired product as a white solid.

Melting point: 253°-254° C.
Isomer purity: Trans form 99% (measured by HPLC)
Elementary analysis (%): as $C_{20}H_{21}NO_3 \cdot \frac{1}{2}C_4H_4 \cdot 1/5$-$H_2O$

|  | C | H | N |
|---|---|---|---|
| Found | 68.74 | 6.35 | 3.61 |
| Calculated | 68.63 | 6.13 | 3.64 |

EXAMPLES 50-59

The products identified in Table 11, the physicochemical properties of which are shown in Table 12 are obtained in the same manner as in Example 49.

TABLE 11

| Compound No. | | |
|---|---|---|
| 5' | Monofumarate · 1/3 hydrate of Compound 5 | (Cis form 99%) |
| 7' | Monofumarate · monohydrate of Compound 7 | (Cis form 70%) |
| 11' | Difumarate · 1/2 hydrate of Compound 11 | (Trans form 100%) |
| 13' | 1/2 Fumarate · 1/2 hydrate of Compound 13 | (Trans form 93%) |
| 15' | Monofumarate of Compound 15 | (Trans form 100%) |
| 20' | Monofumarate · 3/2 hydrate of Compound 20 | (Trans form 95%) |
| 26' | Monofumarate · 2/3 hydrate of Compound 26 | (Trans form 88%) |
| 28' | Monofumarate · 1/2 hydrate of Compound 28 | (Trans form 63%) |
| 31' | 1/2 Fumarate · monohydrate of Compound 31 | (Trans form 95%) |
| 33' | Monofumarate of Compound 33 | (Cis form 100%) |

TABLE 12

| Compound | Melting point (°C.) | Elementary analysis (%) | | | |
|---|---|---|---|---|---|
| 5' | White solid 100 (Decomposition) (Isopropylether) | as $C_{26}H_{29}O_7N \cdot 1/3H_2O$ | | C | H | N |
| | | Found | 66.03 | 6.31 | 2.96 |
| | | Calculated | 66.14 | 6.55 | 3.14 |
| 7' | White solid vague owing to absorption of moisture | as $C_{26}H_{27}O_7N \cdot H_2O$ | | C | H | N |
| | | Found | 64.32 | 6.11 | 2.66 |
| | | Calculated | 64.59 | 6.05 | 2.90 |
| 11' | White solid 266-268 (Isopropanol) | as $C_{30}H_{32}O_{11}N_2 \cdot 1/2H_2O$ | | C | H | N |
| | | Found | 59.55 | 5.44 | 4.53 |
| | | Calculated | 59.50 | 5.49 | 4.63 |
| 13' | White solid 232-235 (Decomposition) (Isopropanol) | as $C_{23}H_{23}O_6N \cdot 1/2H_2O$ | | C | H | N |
| | | Found | 66.63 | 5.83 | 3.44 |
| | | Calculated | 66.72 | 5.85 | 3.44 |
| 15' | White solid 250-254 (Isopropanol) | as $C_{25}H_{25}O_7NS$ | | C | H | N |
| | | Found | 64.21 | 5.59 | 3.73 |
| | | Calculated | 64.23 | 5.39 | 3.99 |
| 20' | White solid 135-138 (Isopropyl ether) | as $C_{25}H_{27}O_7N \cdot 3/2H_2O$ | | C | H | N |
| | | Found | 62.58 | 6.12 | 2.77 |
| | | Calculated | 62.49 | 6.29 | 2.91 |
| 26' | White solid 108-110 (Isopropanol) | as $C_{27}H_{30}O_7N_2 \cdot 2/3H_2O$ | | C | H | N |
| | | Found | 64.15 | 6.47 | 5.24 |
| | | Calculated | 64.02 | 6.24 | 5.53 |
| 28' | White amorphous vague owing to absorption of moisture | as $C_{26}H_{29}NO_7$ | | C | H | N |
| | | Found | 66.58 | 6.61 | 2.82 |
| | | Calculated | 66.80 | 6.25 | 3.00 |
| 31' | White solid vague owing to absorption of moisture (Petroleum ether) | as $C_{23}H_{27}O_4N \cdot H_2O$ | | C | H | N |
| | | Found | 65.53 | 6.81 | 2.96 |
| | | Calculated | 65.39 | 6.92 | 3.32 |
| 33' | White solid 146 (Acetone) | as $C_{26}H_{31}O_6N$ | | C | H | N |
| | | Found | 68.81 | 7.16 | 3.22 |
| | | Calculated | 68.86 | 6.89 | 3.09 |

EXAMPLE 60

Monosodium salt.monohydrate of Compound 35 (Compound 35')

In this example, 1.00 g of 11-(2-diethylaminoethyl)imino-6,11-dihydrodibenz[b,e]oxepin-2-carboxylic acid (Compound 35) is dissolved in 100 ml of methanol and 5.5 ml of 28% sodium methoxide methanol solution is added thereto. After stirring the mixture for one hour, the solvent is distilled away under reduced pressure. The residue is triturated by adding isopropylether and is recovered by filtration to obtain 0.98 g of the desired product as a white solid.

Melting point: vague owing to absorption of moisture
Ratio of isomer: Cin:Anti=1:1
Elementary analysis: as $C_{21}H_{25}O_4N_2Na \cdot H_2O$

|  | C | H | N |
|---|---|---|---|
| Found | 64.23 | 6.62 | 7.01 |
| Calculated | 64.27 | 6.68 | 7.14 |

EXAMPLES 61 and 62

The same procedures as in Example 60 are repeated to obtain the products identified in Table 13, the physicochemical properties of which are shown in Table 14.

TABLE 13

| Compound No. | | |
|---|---|---|
| 43' | Sodium salt of Compound 43 | (Anti form 98%) |
| 45' | Sodium salt · monohydrate of Compound 45 | (Anti form 99%) |

| | Melting point (°C.) | Elementary analysis (%) | | | |
|---|---|---|---|---|---|
| 43' | White solid vague owing to absorption of moisture | as $C_{23}H_{27}O_3N_2Na$ | C | H | N |
| | | Found | 68.46 | 7.00 | 6.88 |
| | | Calculated | 68.64 | 6.76 | 6.96 |
| 45' | White solid 140–145 (Isopropyl ether) | as $C_{21}H_{23}O_3N_2Na \cdot H_2O$ | C | H | N |
| | | Found | 64.11 | 6.57 | 6.99 |
| | | Calculated | 64.27 | 6.42 | 7.14 |

EXAMPLE 63

Tablet

A tablet comprising the following components is prepared in a conventional manner.

| | |
|---|---|
| Trans-11-(3-dimethylaminopropylidene)-6,11-dihydrodibenz[b,e]oxepin-2-carboxylic acid · 1/2 fumarate · 1/5 hydrate (Compound 3'): | 30 mg |
| Lactose: | 60 mg |
| Potato starch: | 30 mg |
| Polyvinyl alcohol: | 2 mg |
| Magnesium stearate: | 1 mg |
| Tar pigment: | q.s. |

EXAMPLE 64

Powder

A powder comprising the following components is prepared in a conventional manner.

| | |
|---|---|
| Trans-11-(3-dimethylaminopropylidene)-6,11-dihydrodibenz[b,e]oxepin-2-acetic acid · monofumarate · 3/2 hydrate (Compound 20'): | 30 mg |
| Lactose: | 270 mg |

EXAMPLE 65

Syrup

A syrup comprising the following components is prepared in a conventional manner.

| | |
|---|---|
| 11-(2-dimethylaminoethyl)imino-6,11-dihydrodibenz[b,e]oxepin-2-acetic acid (Compound 37): | 300 mg |
| Purified sucrose: | 40 g |
| Methyl p-oxybenzoate: | 40 mg |
| Propyl p-oxybenzoate: | 10 mg |
| Strawberry flavor: | 0.1 cc |
| Water is added to the above components until the total valume becomes 100 cc | |

EXAMPLE 66

Methyl 11-(3-morpholinopropylidene)-6,11-dihydrodibenz[b,e]oxepin-2-carboxylate (Compound 55)

The desired product is obtained by substituting (3-morpholinopropyl)-triphenylphosphonium bromide hydrobromide for (3-dimethylaminopropyl)-triphenylphosphonium bromide hydrobromide in Example 5 as a colorless oily matter.

Mass spectrum (m/z): 379 (M+) for $C_{23}H_{25}O_4N$

EXAMPLE 67

Methyl 11-(3-thiomorpholinopropylidene)-6,11-dihydrodibenz[b,e]oxepin-2-carboxylate (Compound 57)

The desired product is obtained by substituting (3-thiomorpholinopropyl)-triphenylphosphonium bromide hydrobromide for (3-dimethylaminopropyl)-triphenylphosphonium bromide hydrobromide in Example 5 as a colorless oily matter.

Mass spectrum (m/z): 395 (M+) for $C_{23}H_{25}O_3NS$

EXAMPLE 68

Methyl trans-3-[11-(3-dimethylaminopropylidene)-6,11-dihydrodibenz[b,e]oxepin-2-yl]-acrylate (Compound 59)

The desired product is obtained by substituting trans-3-(11-oxo-6,11-dihydrodibenz[b,e]oxepin-2-yl)-acrylic acid for 11-oxo-6,11-dihydrodibenz[b,e]oxepin-2-acetic acid in Example 9 as a colorless oily matter.

Mass spectrum (m/z): 363 (M+) for $C_{23}H_{25}O_3N$

EXAMPLE 69

Methyl 11-(3-methylaminopropylidene)-6,11-dihydrodibenz[b,e]oxepin-2-acetate (Compound 61)

The desired product is obtained by substituting (3-methylaminopropyl)-triphenylphosphonium bromide hydrobromide for (3-dimethylaminopropyl)-triphenylphosphonium bromide hydrobromide in Example 9 as a colorless oily matter.

Mass spectrum (m/z): 337 (M+) for $C_{21}H_{23}O_3N$

EXAMPLE 70

Methyl 11-(3-aminopropylidene)-6,11-dihydrodibenz[b,e]oxepin-2-acetate (Compound 63)

The desired product is obtained by substituting (3-aminopropyl)-triphenylphosphonium bromide hydrobromide for (3-dimethylaminopropyl)-triphenylphosphonium bromide hydrobromide in Example 9 as a colorless oily matter.

Mass spectrum (m/z): 323 (M$^+$) for $C_{20}H_{21}O_3N$

EXAMPLES 71-75

11-(3-Morpholinopropylidene)-6,11-dihydrodibenz[b,e]-oxepin-2-carboxylic acid (Compound 56)

11-(3-Thiomorpholinopropylidene)-6,11-dihydrodibenz[b,e]oxepin-2-carboxylic acid (Compound 58)

Trans-3-[11-(3-dimethylaminopropylidene)-6,11-dihydrodibenz[b,e]oxepin-2-yl]-acrylic acid (Compound 60)

11-(3-Methylaminopropylidene)-6,11-dihydrodibenz[b,e]oxepin-2-acetic acid (Compound 62)

11-(3-Aminopropylidene)-6,11-dihydrodibenz[b,e]oxepin-2-acetic acid (Compound 64)

The same hydrolysis procedures as in Example 28 are repeated to obtain the desired products, the physicochemical properties of which are shown in Table 15.

TABLE 15

| Compound | Melting point (°C.) | Elementary analysis (%) or Mass spectrum | | | |
|---|---|---|---|---|---|
| 56 | White solid 130-131 (Decomposition) (Isopropanol) | Cis form 87% as $C_{22}H_{23}O_4N \cdot C_3H_8O$ | | | |
| | | | C | H | N |
| | | Found | 70.65 | 7.34 | 3.27 |
| | | Calculated | 70.57 | 7.34 | 3.29 |
| 58 | White solid 201-205 (Isopropanol) | Cis form 87% 1/2 hydrate as $C_{22}H_{23}O_3NS \cdot 1/2H_2O$ | | | |
| | | | C | H | N |
| | | Found | 67.69 | 6.03 | 3.36 |
| | | Calculated | 67.67 | 6.20 | 3.59 |
| 60 | Colorless oily matter | 394 (M$^+$) for $C_{22}H_{23}O_3N$ | | | |
| 62 | White solid | Cis form 100% | | | |
| | 236-238 (Water) | as $C_{20}H_{21}O_3N$ | | | |
| | | | C | H | N |
| | | Found | 74.01 | 6.60 | 4.01 |
| | | Calculated | 74.28 | 6.55 | 4.33 |
| 64 | White solid 250 (Decomposition) (Water) | Cis form 100% as $C_{19}H_{19}O_3N$ | | | |
| | | | C | H | N |
| | | Found | 73.57 | 6.38 | 4.44 |
| | | Calculated | 73.77 | 6.19 | 4.53 |

EXAMPLE 76

Cis form of monofumarate of Compound 60 (Compound 60') is obtained in the same manner as in Example 49 as a white solid.

Melting point: 176°-178° C. (Isopropanol)
Elementary analysis (%): as $C_{26}H_{27}O_7N$

| | C | H | N |
|---|---|---|---|
| Found | 67.09 | 5.97 | 2.89 |
| Calculated | 67.09 | 5.85 | 3.01 |

What is claimed is:

1. A dibenz[b,e]oxepin compound in cis form having the formula

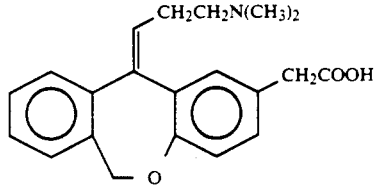

and pharmaceutically acceptable salts thereof.

2. A compound according to claim 1, wherein said salt is selected from the group consisting of acid addition salt, metal salt, ammonium salt, organic amine addition salt, and amino acid addition salt.

3. A pharmaceutical composition comprising a pharmaceutical carrier and as an active ingredient, an effective amount of a dibenz[b,e]oxepin compound defined in claim 1.

* * * * *

UNITED STATES PATENT AND TRADEMARK OFFICE
CERTIFICATE OF CORRECTION

PATENT NO. : 5,116,863
DATED : May 26, 1992
INVENTOR(S) : ETSUO OSHIMA, ET AL.

Page 1 of 3

It is certified that error appears in the above-identified patent and that said Letters Patent is hereby corrected as shown below:

COLUMN 1

Line 64, "$-(CH_2)hd\ s$" should read -- $-(CH_2)s$--.

COLUMN 2

Line 53, "$-(CH_2)hd\ m$" should read -- $-(CH_2)m$--.

COLUMN 19

Line 48, "Methyl trans-11" should read --Trans-11--.

COLUMN 20

TABLE 2, " $X-(CH_2)_n-Z$ " should read --  --.

COLUMN 21

TABLE 2-continued,
" $X-(CH_2)_n-Z$ " should read -- 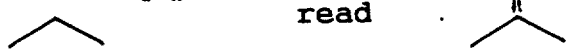 --.

COLUMN 22

TABLE 2-continued,
" $X-(CH_2)_n-Z$ " should read --  --.

UNITED STATES PATENT AND TRADEMARK OFFICE
CERTIFICATE OF CORRECTION

PATENT NO. : 5,116,863
DATED : May 26, 1992
INVENTOR(S) : ETSUO OSHIMA, ET AL.

Page 2 of 3

It is certified that error appears in the above-identified patent and that said Letters Patent is hereby corrected as shown below:

COLUMN 23

TABLE 3, " 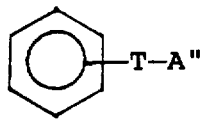     should read   -- 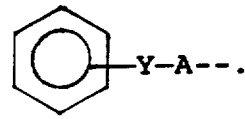 .

Line 30,  "21    5.66    6.02    B"    should read
         --21    5.66    6.02    A--.

COLUMN 24

Lines 26-33, " 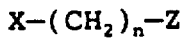
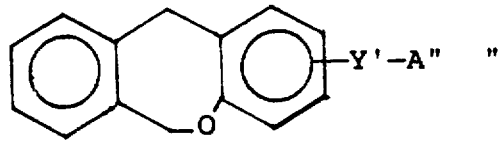 "

should read  -- 
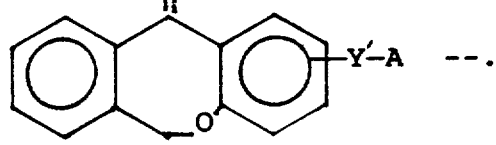 --.

COLUMN 27

TABLE 5-continued, "300    >100" should read --200    >100--.

UNITED STATES PATENT AND TRADEMARK OFFICE
CERTIFICATE OF CORRECTION

PATENT NO. : 5,116,863

DATED : May 26, 1992

INVENTOR(S) : ETSUO OSHIMA, ET AL.

It is certified that error appears in the above-identified patent and that said Letters Patent is hereby corrected as shown below:

COLUMN 43

Line 44, "5.115(bs," should read --5.15(bs,--.

Signed and Sealed this

Fourteenth Day of September, 1993

Attest:

BRUCE LEHMAN

Attesting Officer     Commissioner of Patents and Trademarks

UNITED STATES PATENT AND TRADEMARK OFFICE

CERTIFICATE EXTENDING PATENT TERM
UNDER 35 U.S.C. § 156

PATENT NO.      :   5,116,863

ISSUED          :   May 26, 1992

INVENTOR(S)     :   Etsuo Oshima et al.

PATENT OWNER    :   Kyowa Hakko Kogyo Co., Ltd.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 571 days from May 26, 2009, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 27th day of August 1998.

Bruce A. Lehman
Assistant Secretary of Commerce and
Commissioner of Patents and Trademarks